US011779196B2

(12) United States Patent
Reydel

(10) Patent No.: US 11,779,196 B2
(45) Date of Patent: Oct. 10, 2023

(54) GASTROINTESTINAL ENDOSCOPY WITH ATTACHABLE INTESTINE PLEATING STRUCTURES

(71) Applicant: VISUALIZATION BALLOONS, LLC, West Caldwell, NJ (US)

(72) Inventor: Boris Reydel, West Caldwell, NJ (US)

(73) Assignee: VISUALIZATION BALLOONS, LLC, West Caldwell, NJ (US)

(*) Notice: Subject to any disclaimer, the term of this patent is extended or adjusted under 35 U.S.C. 154(b) by 45 days.

(21) Appl. No.: 16/578,693

(22) Filed: Sep. 23, 2019

(65) Prior Publication Data

US 2020/0015660 A1 Jan. 16, 2020

Related U.S. Application Data

(63) Continuation of application No. 15/121,216, filed as application No. PCT/US2015/016901 on Feb. 20, 2015, now Pat. No. 10,463,235.
(Continued)

(51) Int. Cl.
*A61B 1/00* (2006.01)
*G02B 23/24* (2006.01)
(Continued)

(52) U.S. Cl.
CPC ........ *A61B 1/00082* (2013.01); *A61B 1/0014* (2013.01); *A61B 1/00096* (2013.01);
(Continued)

(58) Field of Classification Search
CPC ............ A61B 1/00082; A61B 1/00101; A61B 1/00131; A61B 1/00135; A61B 1/00089;
(Continued)

(56) References Cited

U.S. PATENT DOCUMENTS 3,417,745 A 12/1968 Emanuel
3,690,769 A 9/1972 Mori
(Continued)

FOREIGN PATENT DOCUMENTS

EP 0112148 6/1984
EP 2575590 4/2013
(Continued)

OTHER PUBLICATIONS

International Search Report and Written Opinion of the International Searching Authority for Application No. PCT/US2015/016901, dated Jul. 8, 2015, 15 pages.
(Continued)

*Primary Examiner* — Ryan N Henderson
*Assistant Examiner* — Pamela F Wu
(74) *Attorney, Agent, or Firm* — Meunier Carlin & Curfman LLC

(57) ABSTRACT

Disclosed herein are intestine pleating attachable structures for use with endoscopes and methods for using said structures. The intestine pleating attachable structures may act in conjunction with a gastrointestinal endoscope and, optionally, a balloon to improve visualization during endoscopic procedures. The intestine pleating attachable structures are coupled to the endoscope shaft, and include at least one flexible appendage to enhance contact between the structure and the intestinal wall. When the endoscope is retracted, the flexible appendage assists in moving the intestinal wall relative to the imaging system. This movement causes the intestine to pleat. Pleating reduces looping, improves efficiency, and results in a less painful endoscopic procedure for the patient. The attachable structures may be used in conjunction with a dome-shaped balloon that is inflated at the distal, imaging end of the endoscope. The balloon is transparent, such that the intestinal wall may still be visualized
(Continued)

through the balloon while intestinal matter is prevented from obscuring the image.

19 Claims, 27 Drawing Sheets

Related U.S. Application Data

(60) Provisional application No. 61/966,403, filed on Feb. 24, 2014.

(51) Int. Cl.
*A61B 1/31* (2006.01)
*A61M 25/00* (2006.01)
*A61B 1/05* (2006.01)

(52) U.S. Cl.
CPC ...... *A61B 1/00131* (2013.01); *A61B 1/00135* (2013.01); *G02B 23/24* (2013.01); *G02B 23/2476* (2013.01); *A61B 1/05* (2013.01); *A61B 1/31* (2013.01); *A61M 25/0067* (2013.01)

(58) Field of Classification Search
CPC ..... A61B 1/0014; A61B 1/00156; A61B 1/31; A61B 1/0008; A61B 1/00071; A61B 1/00112; A61B 1/00121; A61B 1/00137; A61B 1/00142; A61B 1/00154; A61M 25/04; A61M 29/00; A61M 25/10; A61M 25/1018; A61M 2025/1015; A61M 2025/1054; G02B 23/2476
USPC ................................. 604/198; 600/114–116
See application file for complete search history.

(56) References Cited

U.S. PATENT DOCUMENTS

| | | | |
|---|---|---|---|
| 3,866,599 A | | 2/1975 | Johnson |
| 4,207,872 A | | 6/1980 | Meiri et al. |
| 4,619,247 A | | 10/1986 | Inoue et al. |
| 4,681,093 A | | 7/1987 | Ono et al. |
| 4,841,952 A | | 6/1989 | Sato et al. |
| 4,881,810 A | | 11/1989 | Hasegawa |
| 4,961,738 A | | 10/1990 | Mackin |
| 5,002,556 A | | 3/1991 | Ishida et al. |
| 5,029,574 A | | 7/1991 | Shimamura et al. |
| 5,103,804 A | | 4/1992 | Abele et al. |
| 5,257,617 A | | 11/1993 | Takahashi |
| 5,271,383 A | | 12/1993 | Wilk |
| 5,304,173 A | | 4/1994 | Kittrel et al. |
| 5,337,730 A | | 8/1994 | Maguire |
| 5,364,353 A | | 11/1994 | Corfitsen et al. |
| 5,681,344 A | | 10/1997 | Kelly |
| 5,855,569 A | | 1/1999 | Komi |
| 5,897,487 A | | 4/1999 | Ouchi |
| 6,059,719 A | | 5/2000 | Yamamoto et al. |
| 6,306,081 B1 | | 10/2001 | Ishikawa et al. |
| 6,423,055 B1 | | 7/2002 | Farr et al. |
| 6,589,213 B2 | | 7/2003 | Reydel |
| 6,767,339 B2 | | 7/2004 | Reydel |
| 6,953,431 B2 | | 10/2005 | Barthel |
| 8,574,289 B2 | | 11/2013 | Cartledge et al. |
| 9,220,396 B2 | | 12/2015 | Reydel |
| 2002/0068853 A1 | | 6/2002 | Adler |
| 2003/0233142 A1 | | 12/2003 | Morales et al. |
| 2004/0077926 A1 | | 4/2004 | Moriyama |
| 2005/0049461 A1 | | 3/2005 | Honda et al. |
| 2005/0288552 A1 | | 12/2005 | Barthel |
| 2006/0025654 A1 | | 2/2006 | Suzuki et al. |
| 2006/0106414 A1 | | 5/2006 | Fogarty et al. |
| 2006/0287666 A1* | 12/2006 | Saadat ............... | A61M 25/1011 606/198 |
| 2007/0015966 A1 | | 1/2007 | Niwa et al. |
| 2007/0123798 A1* | 5/2007 | Rahamimov ...... | A61B 17/3431 600/564 |
| 2007/0225651 A1* | 9/2007 | Rosenberg ............ | A61M 25/04 604/174 |
| 2007/0249907 A1 | | 10/2007 | Boulais et al. |
| 2007/0010785 A1 | | 11/2007 | Sekiguchi et al. |
| 2007/0276180 A1 | | 11/2007 | Greenburg et al. |
| 2007/0287885 A1 | | 12/2007 | Brown |
| 2008/0249358 A1* | 10/2008 | Motai ................ | A61B 1/00006 600/115 |
| 2008/0306467 A1 | | 12/2008 | Reydel |
| 2009/0082626 A1 | | 3/2009 | Ichimura et al. |
| 2009/0287050 A1 | | 11/2009 | Barthel |
| 2010/0145278 A1* | 6/2010 | Magana ................ | A61M 25/04 604/164.01 |
| 2010/0274084 A1 | | 10/2010 | Barthel |
| 2011/0009696 A1 | | 1/2011 | Miyoshi |
| 2011/0251458 A1* | 10/2011 | Terliuc ................... | A61B 8/445 600/116 |
| 2012/0197083 A1 | | 8/2012 | Spenser |
| 2012/0232342 A1 | | 9/2012 | Reydel |
| 2012/0259175 A1 | | 10/2012 | Reydel et al. |
| 2013/0023854 A1* | 1/2013 | Reydel ............. | A61B 17/22031 604/528 |
| 2013/0090527 A1* | 4/2013 | Axon ................ | A61B 1/00075 600/114 |
| 2015/0148606 A1* | 5/2015 | Rottenberg ........ | A61B 1/00101 600/114 |

FOREIGN PATENT DOCUMENTS

| | | |
|---|---|---|
| EP | 3079558 | 10/2016 |
| JP | 63201504 | 12/1988 |
| JP | 01/221133 | 9/1989 |
| JP | 2003/033319 | 2/2003 |
| JP | 2003180611 A | 7/2003 |
| JP | 2003/339631 | 12/2003 |
| JP | 2005/503203 | 2/2005 |
| JP | 2007/175502 | 7/2007 |
| JP | 2008/212506 | 9/2008 |
| JP | 2009/534113 | 9/2009 |
| WO | 2011/047339 | 4/2011 |
| WO | 2012/138815 | 10/2012 |
| WO | 2014/123563 | 8/2014 |
| WO | 2015/160970 | 10/2015 |

OTHER PUBLICATIONS

International Search Report and Written Opinion for International Application No. PCT/US14/70049, dated Mar. 18, 2015, 9 pages.
Office Action from European Application No. 10824218.1 dated Mar. 1, 2013.
English Translation of Office Action for Japanese Application No. 2012-534419 dated Feb. 18, 2014.
International Search Report and Written Opinion from International Application No. PCT/US2010/052947, dated May 27, 2011, 6 pages.
U.S. Appl. No. 14/583,283, filed Nov. 11, 2014, and the prosecution history thereof.
U.S. Appl. No. 14/568,993, filed Dec. 12, 2014, and the prosecution history thereof.
U.S. Appl. No. 13/501,803, filed May 24, 2012, and the prosecution history thereof.
International Preliminary Report on Patentability issued by the International Bureau of WIPO, Application No. PCT/US2015/016901, dated Sep. 9, 2016, 12 pages.
International Search Report and Written Opinion for International Application No. PCT/US2012/032248, dated Jul. 2, 2012, 14 pages.
International Search Report and Written Opinion for International Application No. PCT/US2015/026000, dated Sep. 24, 2015, 18 pages.
International Preliminary Report on Patentability issued by the International Bureau of WIPO, Application No. PCT/US2015/026000, dated Oct. 27, 2016, 12 pages.

(56) References Cited

OTHER PUBLICATIONS

Extended European Search Report issued for European Application No. 15752011.5, dated Sep. 20, 2017.
European Patent Office. Communication pursuant to Rule 94(3) EPC. Issued in European Application No. 15752011.5 dated Mar. 20, 2019. 5 pages.
Extended European Search Report issued by the European Patent Office in European Application No. 157804840.0 dated Nov. 30, 2017, 11 pages.
Machine translation of JP 63201504 (foreign patent document #1, above); accessed Nov. 16, 2021.
European Office Action, in connection with European Application No. 15752011.5, dated Jul. 11, 2022.
"Randomized controlled trail of EndoRings assisted colonoscopy versus standard colonoscopy" Digestive Endoscopy 2022. pp. 1-7.

\* cited by examiner

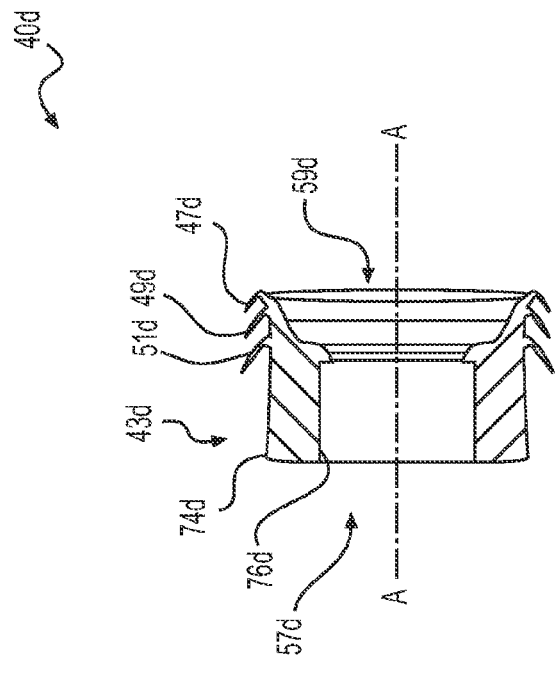
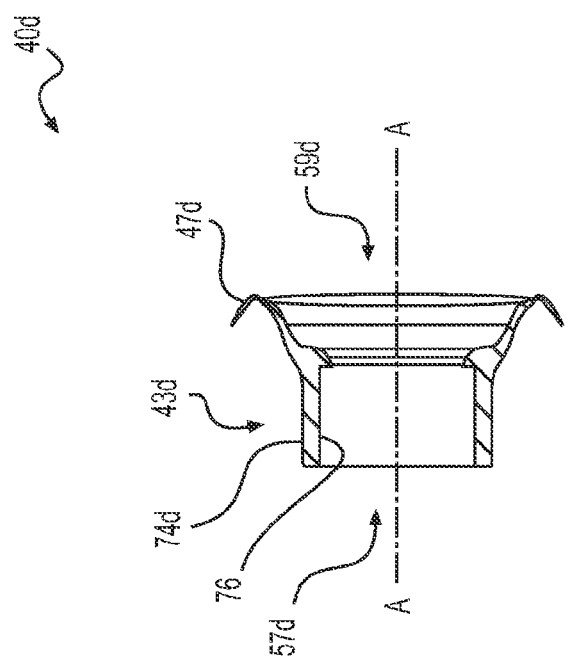

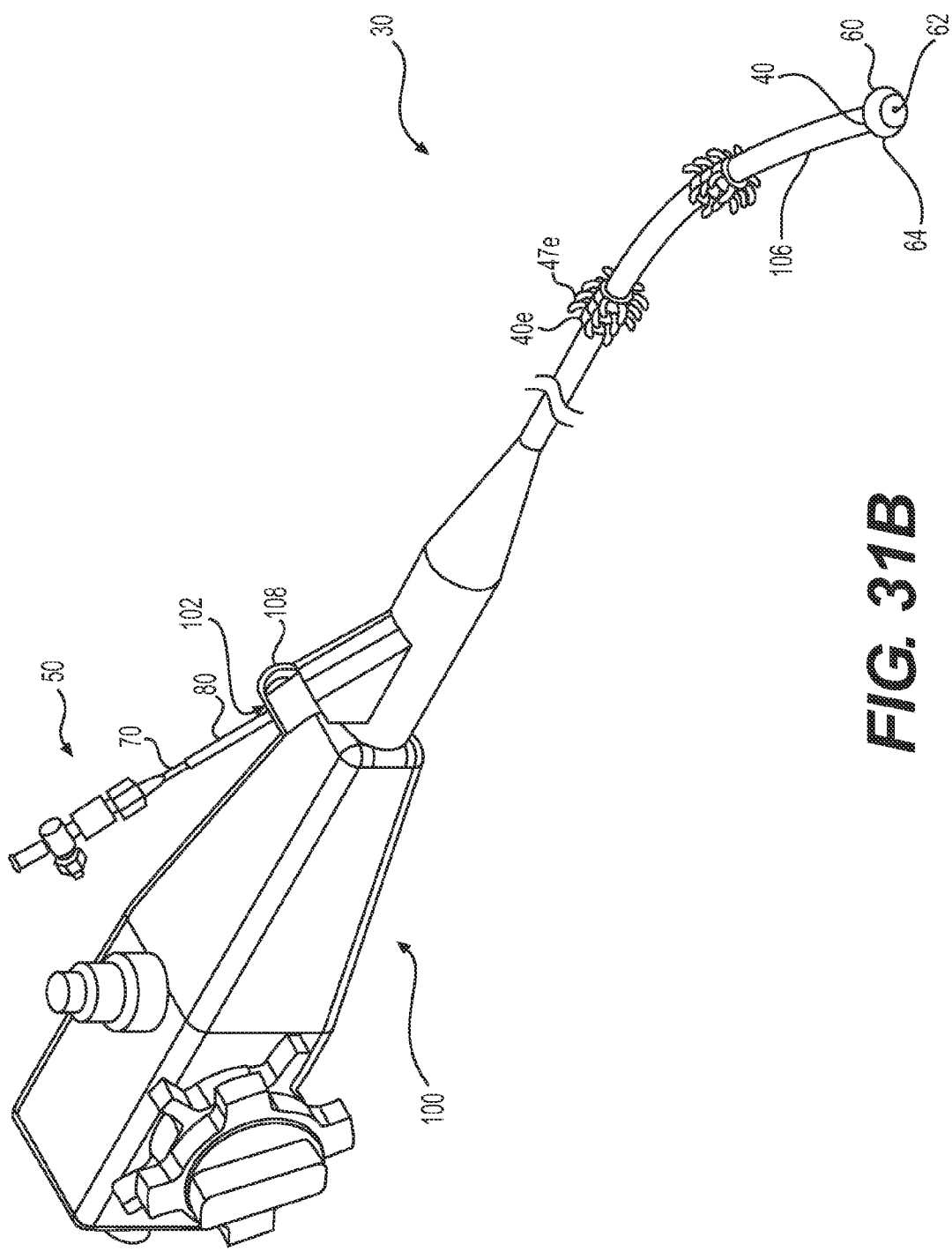

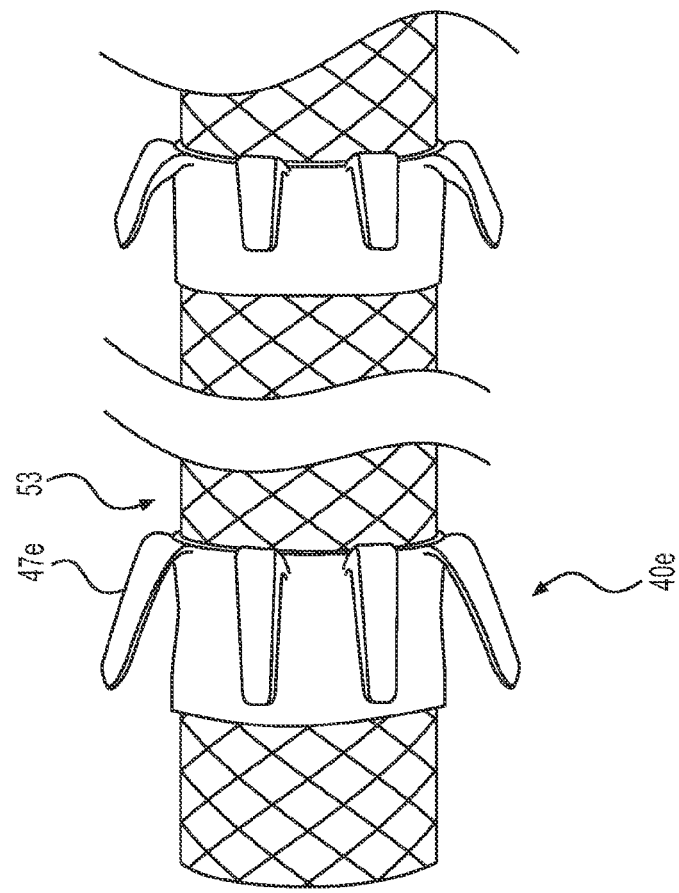
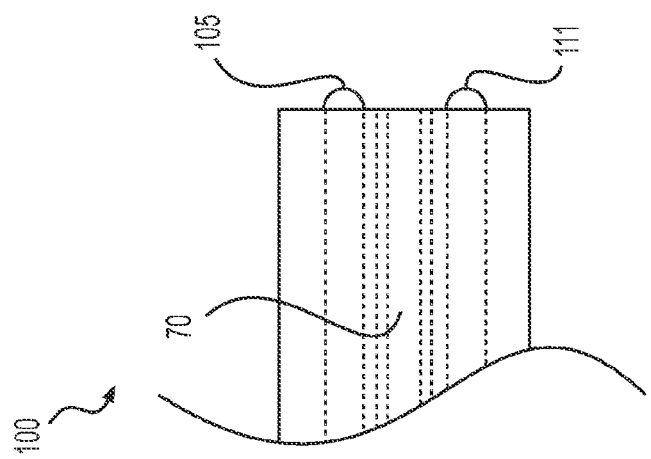
FIG. 32

GASTROINTESTINAL ENDOSCOPY WITH ATTACHABLE INTESTINE PLEATING STRUCTURES

RELATED APPLICATIONS

This application is a continuation of U.S. application Ser. No. 15/121,216, filed Aug. 24, 2016, which is a national stage application filed under 35 U.S.C. § 371 of PCT/US2015/016901, filed Feb. 20, 2015, which claims the benefit of and priority to U.S. Provisional Application 61/966,403, filed Feb. 24, 2014, the disclosures of which are expressly incorporated herein by reference in their entireties.

TECHNICAL FIELD

The present apparatus embodied relates, in general, to medical devices and in particular, to gastrointestinal endoscopy with attachable intestine pleating structures.

BACKGROUND

Endoscopes are well-known in the art and are flexible devices that are inserted into a natural body orifice such as the mouth or anus to provide visual and surgical access to portions of the upper and lower gastrointestinal (GI) tract. Endoscope accessible portions of the lower GI tract extend front the anus to the small intestine, and during this journey, the flexible endoscope must traverse a torturous convoluted path through the anus, the rectum, and through the large intestine to the ileocecal opening of the small intestine. The torturous path includes "S" shaped passage through the rectosigmoid junction and the sigmoid colon, and around several larger than right angled bends of the splenic flexure and hepatic flexure. Additionally, in small bowel enteroscopy, an endoscope must traverse a large torturous convoluted path having multiple "S" shaped passages.

Before insertion of the endoscope, the patient is given drugs to purge fecal matter from the lower GI tract. Once emptied, the tubular walls of the large intestine can flatten or collapse together into a flattened tubular configuration. The collapsed intestines may inhibit passage of the flat face of the distal end of the endoscope, and the collapsed tissue can inhibit visualization by pressing against or near to a camera mounted within the flat face. To enhance the passage of the endoscope through the collapsed lower GI tract and to improve visualization, insufflation gas is routinely pumped into the patient's lower GI tract to expand and distend the collapsed tubular tissues. The expanded walls may improve visualization and reduce tissue contact with the flat face of the endoscope as it is pushed farther and farther into the insufflated lower GI tract. The distal portion of the endoscope is steerable, and the insufflated tissue can provide room for the surgeon to visually steer the endoscope through the path ahead.

The administration of insufflation gas to the lower GI tract can induce abdominal discomfort, and this has led to the common practice of anesthetizing the patient during the procedure. Additionally, insufflation gas may cause lengthening of anatomy and spontaneous perforation. Post-surgical recovery times are provided to allow the patient to purge insufflation gas and to awaken from the anesthesia. $CO_2$ is commonly used for insufflation as it is more readily absorbed through the patient's intestinal wall to reduce the post-operative recovery time. $CO_2$ gas control systems, $CO_2$ tanks, and $CO_2$ gas heaters must be purchased and maintained in order to provide $CO_2$ as an insufflation gas.

In general, a complete colonoscopy requires the physician to advance the colonoscope into the colon, negotiate the sigmoid colon, and left and right colic flexures up to the cecum. Advancement of the endoscope is generally accomplished by manipulation of a steerable tip of the endoscope, which is controlled at the proximal end of the device by the physician, in addition to torquing and pushing the endoscope forward or pulling it backward.

Problems regularly occur, however, when negotiating the endoscope through the bends of the colon, such as at the sigmoid and left and right colic flexures. These problems arise because the colon is soft and has unpredictable fixation points to the viscera of the abdomen, and it is easily distensible. Consequently, after the steerable tip of the endoscope is deflected to enter a new region of the colon, the principal direction of the force applied by the physician urging the end of the device into the patients colon is not in the direction of the steerable tip. Instead, the force is directed along the axis of the endoscope and towards the preceding bend(s), and causes yielding or displacement of the colon wall. This problem, also known as looping, causes the colon to take a non-native shape.

The loads imposed by the endoscope on the colon wall can have a myriad of possible effects, ranging from patient discomfort to spastic cramp-like contractions of the colon and even possible perforation or dissection of the colon. Consequently, the endoscope cannot be advanced as far as the cecum in a significant number of cases.

SUMMARY

During an endoscopic procedure, removal of an intestinal loop is typically accomplished by retracting the endoscope, then pushing forward again. This pushing and pulling pleats the intestine, creating folds behind the tip of the endoscope and flattening the wall in front of the tip. This flattening has the additional benefit of improving visualization of the adjacent intestinal wall. Disclosed herein are intestine pleating attachable structures for use with gastrointestinal endoscopes and methods for using said structures. As used herein, the term "endoscope" is defined as a gastrointestinal endoscope.

The intestine pleating structures act in conjunction with an endoscope and, optionally, a balloon, to improve visualization during endoscopic procedures. During such a procedure, the intestinal pleating structures are coupled to the endoscope shaft. The attachable structures may include at least one flexible appendage to enhance contact between the structure and the intestinal wall. When the endoscope is retracted, the flexible appendage assists in moving the intestinal wall relative to the imaging system. This movement reduces looping, improves efficiency, and results in a less painful endoscopic procedure for the patient. Contact between the attachable structure and the intestinal wall is enhanced when the patient is not insufflated during the procedure.

The intestine pleating attachable structures include a body having an inner surface and an outer surface. The inner surface of the body defines a passageway for passage of an endoscope. The passageway of the body has a proximal opening, a distal opening, and a central longitudinal axis extending through the passage. One or more flexible appendages may extend from the outer surface of the body. The appendages are biased toward the proximal opening of the body in a first position at a first acute angle relative to the longitudinal axis of the body. The first acute angle is less than 50 degrees. For example, the appendages may be biased toward the proximal opening of the body at 35 degrees in the first position.

The appendages are movable to a second position, in which the appendage tips point away from the proximal opening at a second acute angle relative to the longitudinal axis. The greatest width of the attachable structure, measured perpendicular to the longitudinal axis and extending from a first appendage tip on one side of the longitudinal axis to a second appendage tip on the other side of the longitudinal axis, is up to and including 33 millimeters.

In some embodiments, the body is a substantially continuous piece of material. The flexible appendages may be continuous with the flexible body. For example, the flexible appendages and the flexible body may be a continuous piece of the same material. In other embodiments, the body of the attachable structure is relatively less flexible than the flexible appendages. Thermoplastic elastomers may be used to form the attachable structures. In other embodiments, the structures may be formed of silicone.

The attachable structure has a length measured parallel to a longitudinal axis of the body. In some embodiments, the length is between 1-20 millimeters. Some embodiments of the body opening have radii between 2-8 millimeters. Some embodiments of the body opening have a cross-sectional area between 12-201 $mm^2$.

The flexible appendages of the attachable structures have lengths between 1-5 millimeters from an outer surface. The appendages may be aligned to each other with respect to their position along the body of the attachable structure, forming at least one row of flexible appendages. In some embodiments, a row may comprise up to twenty appendages. In other embodiments, a row may comprise more than twenty appendages. Some attachable structures may have multiple rows of flexible appendages. The lengths of the flexible appendages, as measured extending outwardly from the body of the attachable structure, may vary from row to row. For example, the flexible appendages of a first row may be shorter than the lengths of the appendages on a proximally spaced row. Alternatively, the lengths of the flexible appendages may be the same regardless of the row.

The flexible appendages of the attachable structures include base portions adjacent the flexible body and outer portions spaced outwardly from the base portions. The outer portions of the appendages culminate in appendage tips. The flexible appendages may also include top faces that are oriented toward the distal opening of the body. The width across the top face of a flexible appendage may be narrower at the base portion than the outer portion. In some embodiments, the width across the top face is at least twice the distance as a thickness measured perpendicular to the top face. The thickness of a flexible appendage, as measured perpendicularly from the top face, is between 0.1-0.9 millimeters.

Some attachable structures may be tubular and comprise a lumen. Some may take the form of a cap that is configured to be coupled to the distal end of an endoscope. In some embodiments, the attachable structure is configured to stretch around the shaft of an endoscope. The structure may be configured to be rolled up the shaft of the endoscope in certain implementations.

Some attachable structures may be configured to extend around a portion of an endoscope shaft. For example, they may extend 90-360° around an endoscope shaft. In some implementations, the attachable structure may include a clip for attachment to the shaft of an endoscope. These embodiments may also include fastening mechanisms for securing the clip to the shaft. The fastening mechanism, in some embodiments, may include a hinge.

Some attachable structures are movable along the endoscope shaft. Some embodiments include an elongate sheath configured to fit tightly around the shaft of an endoscope. In some embodiments, the sheath is the body of the attachable structure. In others cases, one or more bodies of attachable structures may be positioned radially outward from the sheath. The sheath, in some implementations, may be a mesh.

A balloon access device for use with an endoscope is also disclosed herein. The endoscope comprises a shaft extending between proximal and distal ends. An imaging system may be located partially located on a distal face of the endoscope. The imaging system includes an illumination system, also located at least partially on the distal face of the endoscope.

The balloon access device further includes a balloon that is configured to be positioned at a distal end of an endoscope. The balloon is expandable from a deflated shape to an inflated shape. It includes a proximal end and a distal end having a dome portion. A portion of the proximal end may be positioned over a component of the imaging system when the balloon is positioned at the endoscope distal end and in its inflated shape, such that imaging using the endoscope comprises the transmission of light through the proximal and distal ends of the balloon. The component of the imaging system may include a lens or a camera.

The balloon access device further includes at least one of the aforementioned attachable structures. The attachable structure of the balloon access device is configured to induce intestinal pleating when an inserted endoscope is pulled back toward an opening of a bodily cavity. These structures are configured to be coupled to the endoscope, either at the distal end and/or along the shaft. The attachable structure includes a body having a proximal end and a distal end, an opening extending between the proximal and distal ends, and at least one flexible appendage extending outwardly from the body. At least one attachable structure contacts the balloon when the balloon is positioned at the endoscope distal end and in its inflated shape, such that imaging using the endoscope comprises transmission of light through the proximal and distal ends of the balloon.

The balloon of the balloon access device may be configured to seal with the attachable structure. The attachable structure may include a balloon sealing portion proximate to its distal end. The balloon sealing portion may have a circular groove that retains and seals with a circular rib of the balloon. In some embodiments, the inner portion of the attachable structure may include a rib and a balloon sealing portion, and the proximal end of the balloon contacts the balloon sealing portion and the rib. In other embodiments, the attachable structure body may include an outwardly flaring balloon sealing portion, which prevents the balloon from being unseated from the attachable structure. The at least one flexible appendage may extend outwardly from the balloon sealing portion. In still other embodiments, the proximal end of the balloon may include a collar with at least one engaging portion that is configured to engage the attachable structure adjacent the distal end of the endoscope.

The attachable structure of the balloon access device may include an endoscope receptacle for receiving the distal end of the endoscope. The receptacle may extend into the attachable structure through its proximal end. It may include a stop that engages the front face of the endoscope when the endoscope is received within the attachable structure. The opening may extend through the stop to distally expose at least one component of the imaging system on the distal face of the endoscope.

Multiple attachable structures may be spaced along the shaft of the endoscope. In some embodiments, the length of the flexible appendages of the attachable structure at the distal most point along the endoscope shaft is shorter than the lengths of appendages of at least one of the other attachable structures. For example, the lengths of the flexible appendages of the attachable structures increase moving proximally along the endoscope shaft. In some embodiments, the length of the flexible appendages of au attachable structure is 0.1-1 mm shorter than the flexible appendages of a proximally spaced attachable structure.

Methods of visualizing the internal surface of an intestinal cavity using intestine pleating attachable structures are also disclosed. The methods includes providing at least one attachable structure that may be attached to an endoscope shaft. The method furthers include attaching the attachable structure to the endoscope such that it extends at least partially around the shaft of an endoscope, with the flexible appendage(s) extending outwardly from the shaft of the endoscope.

Methods for visualizing the internal surface of an intestinal cavity include positioning the endoscope within an intestinal cavity of a subject, such that the flexible appendage of the attachable structure contacts the intestinal wall. The method may further include pushing on the shaft of the endoscope to cause a forward advance of the distal end of the endoscope within the intestinal cavity, and pulling back on the shaft of the endoscope. The step of pulling back causes the flexible appendage to move the intestinal wall relative to the imaging system component located on the distal face of the endoscope. This may reduce looping of the intestine.

Methods for visualizing the internal surface of an intestinal cavity may further include promoting contact between the flexible appendage and the intestinal wall. Promoting contact may include performing the method without insufflation of the intestinal cavity.

Attaching the at least one attachable structure may include stretching the attachable structure around the shaft of the endoscope. It may also include positioning one or more attachable structures along the shaft of the endoscope, spaced proximally front the attachable structure located adjacent the distal face of the endoscope. This may be accomplished by rolling the attachable structures proximally along the shaft. In other embodiments, an elongate sheath may be included. The elongate sheath may fit tightly around the shaft of the endoscope, and the attachable structures may be attached to the outside of the sheath. In these embodiments, positioning one or more attachable structures along the shaft of the endoscope comprises positioning the sheath around the shaft. This may be accomplished by pulling the sheath over the distal face of the endoscope, for example.

Pulling back on the shaft of the endoscope may include moving the intestinal wall relative to the imaging system component, and dragging the intestinal wall into a pleated formation. This pleated formation may facilitate a forward advance of the distal face of the endoscope. The step of pulling back on the shaft of the endoscope causes the flexible appendage to flip directions. Methods for visualizing the internal surface of an intestinal cavity may further include pushing the endoscope forward, for example, beyond the pleated formation, after pulling back on the shaft of the endoscope. This forward movement may cause the flexible appendage to flip directions.

Methods for visualizing the internal surface of an intestinal cavity may further include activating the endoscope imaging system to provide visual images of the intestinal wall to a user. A balloon may be provided for inflation adjacent the distal end of the endoscope. The methods may include positioning the balloon over the imaging component of the endoscope, such that activating the imaging system causes light to be transmitted and received through distal and proximal ends of the balloon. When a balloon is provided, the attachable structure may be a cap configured to encircle the distal end of the endoscope. Positioning the balloon over the imaging component of the endoscope may include making contact between the cap and the balloon.

DESCRIPTION OF DRAWINGS

FIG. 28A is a cross section of an attachable structure with a single row of flexible appendages.

FIG. 28B is a cross section of an attachable structure with multiple rows of flexible appendages.

FIG. 31B is an isometric view of an endoscope and balloon access device utilizing groupings of attachable structures with flexible appendages.

FIG. 32 is a side view of an endoscope with attachable structures having flexible appendages. This embodiment also includes a sheath to aid positioning of the attachable structures along the endoscope shaft.

DETAILED DESCRIPTION

The following description of certain examples of the medical apparatus should not be used to limit the scope of the medical apparatus. Other examples, features, aspects, embodiments, and advantages of the medical apparatus will become apparent to those skilled in the art from the following description, which is by way of illustration, one of the best modes contemplated for carrying out the medical apparatus. As will be realized, the medical apparatus is capable of other different and obvious aspects, all without departing from the spirit of the medical apparatus. Accordingly, the drawings and descriptions should be regarded as illustrative in nature and not restrictive.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Figure 1:
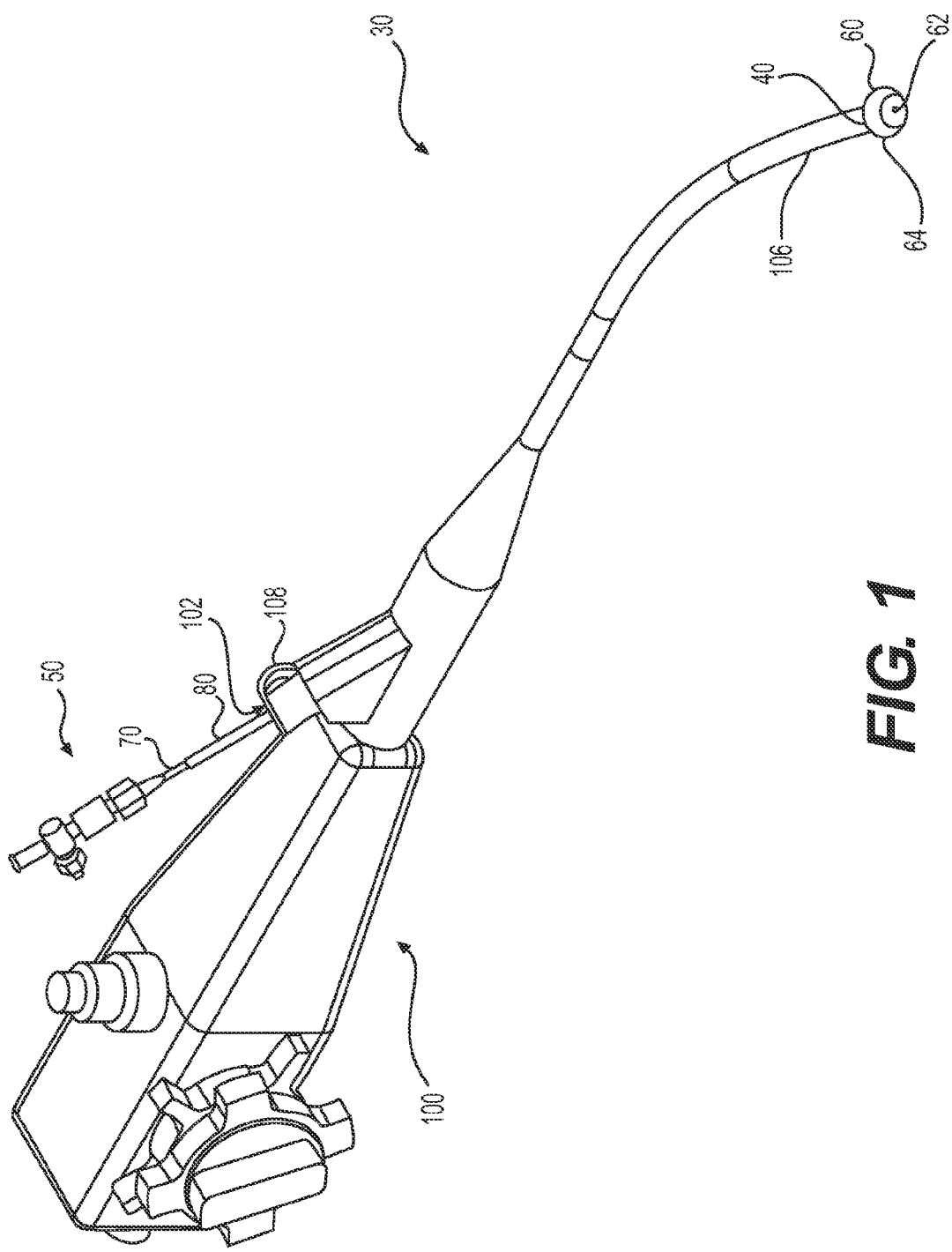
FIG. 1 is an isometric view of an embodiment of a transparent balloon access device deployed on an endoscope.

FIG. 1 is an isometric view of one embodiment of a balloon access device 30 installed upon an endoscope 100. The balloon access device 30 is configured to fit within an operative channel 102 of the endoscope 100 when undeployed, and to deploy a transparent hollow balloon 60 across a distal face 104 of the endoscope 100. The balloon 60 is transparent so that scope optics can view GI tissue there through, and balloon 60 can be dome shaped on at least a distal end. A distally located guide tip 62 is supported solely on a distal end of the dome shape by a membrane wall 65 of the balloon 60. The configuration of the deployed guide tip 62 and balloon 60 on the endoscope 100 is such that non-insufflated GI tissue can be parted and spread with the tip 62 and the balloon 60 in response to pushing with the endoscope 100. The balloon access device 30 and endoscope 100 as configured can rapidly burrow along a non-insufflated and at least partially pinched GI tract such as the non-insufflated lower GI tract, or can pass through an expanded or insufflated portion of the GI tract. As will be described in detail later, the deployed transparent guide tip 62 can be visually aimed at a center of the collapsed lumen of the non-insufflated GI tract by articulating a distal end 106 of the endoscope 100. When the guide tip 62 is aimed, pushing the endoscope 100 initiates the spreading and parting of the collapsed tissue walls with the balloon access device 30, thereby enabling passage of the endoscope 100 along a center of the non-insufflated lumen of the GI tract.

As shown in FIG. 1, the balloon access device 30 is shown inserted into an operative channel 102 of the endoscope 100 and comprises a proximal handle portion 50 extending from a proximal opening of the operative channel 102. A biopsy valve 108 is provided on the proximal opening, of the operative channel 102 and a hollow catheter 70 extends from the proximal handle portion 50, through the biopsy valve 108, and into the operative channel 102. A distal end of the catheter 70 is secured to a proximal end of the transparent balloon 60 shown extending across a distally located front face 104 of the endoscope 100.

A balloon seal cap 40 of the balloon access device 30 is removably secured to the distal end 106 of the endoscope 100 and forms a fluid tight seal with at least one surface on a proximal end of the balloon 60. Alternatively, it will be appreciated that the cap 40 may be integral with the endoscope. The seal cap 40 may be any suitable shape, such as cylindrically shaped. The sealing interaction of the seal cap 40 with the endoscope 100, and the balloon 60 with the seal cap 40, can create a sealed volume across the front face 104 of the endoscope 100 to prevent the egress of unwanted fluids across the optical lens 105 of an endoscope camera located on the front face 104 (see FIG. 17). Additionally, once the seal is formed, the balloon 60 can be further secured to the seal cap 40 by applying a vacuum to the operative channel 102 to draw the balloon 60 into further engagement with the seal cap 40. Alternately, a vacuum port (not shown) in the endoscope 100 can be used to draw the balloon 100 against the front face 104 of the endoscope. The balloon device 30 can be rapidly deployed and inflated into place on the endoscope 100 for advancement, and rapidly deflated and withdrawn from the operative channel 102 of the endoscope 100 for the insertion and deployment of another surgical instrument from the operative channel 102 into the lower GI tract. An example of such another surgical instrument can be, but is not limited thereto, a snare or tissue biopsy device to retrieve a tissue sample from a suspect site.

Figure 2:
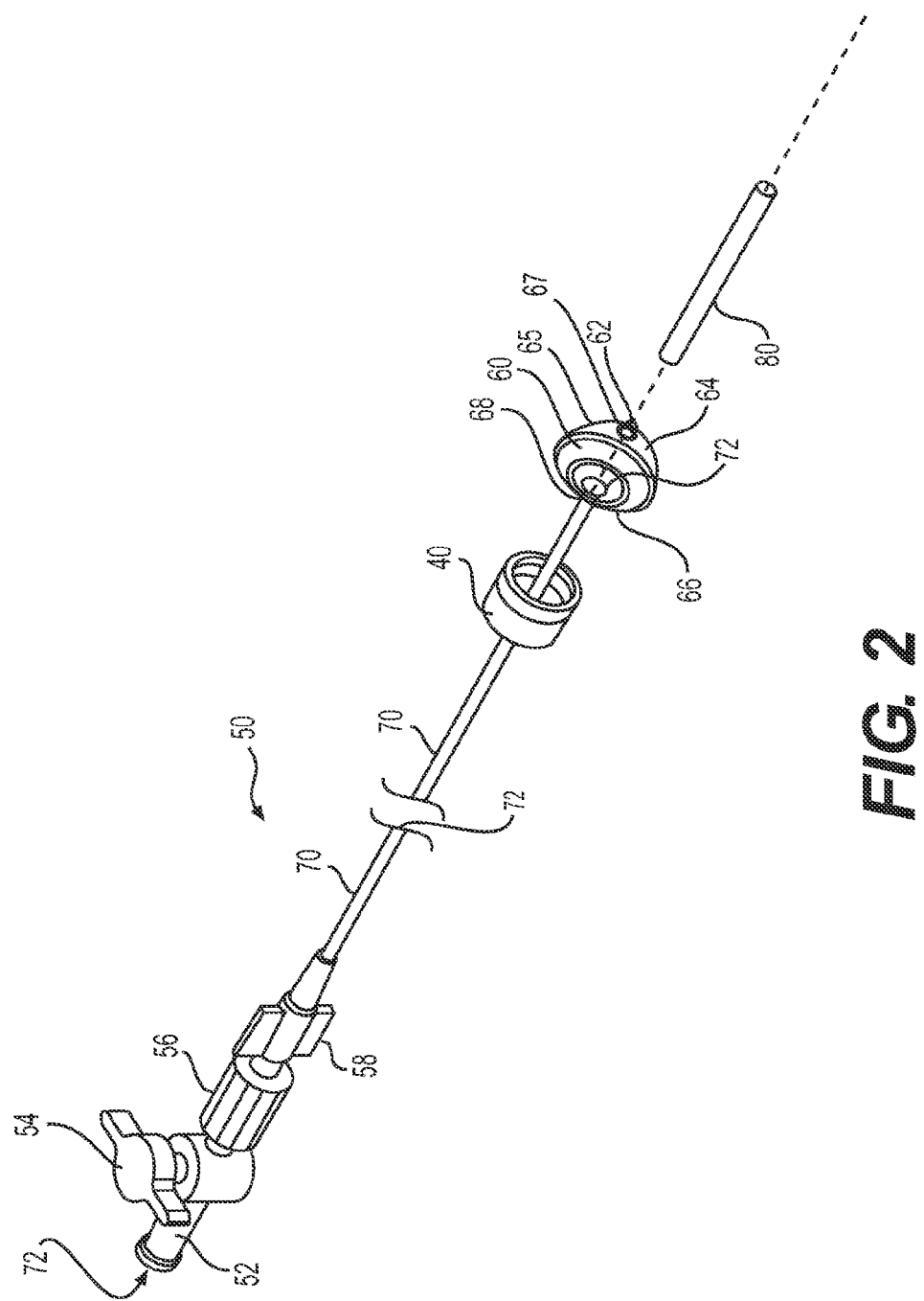
FIG. 2 is an isometric view of the balloon access device with the transparent balloon shown in a normal unexpanded dome shape.

FIG. 2 shows an isometric view of the balloon access device 30. The handle or proximal handle portion 50 includes a hollow passage 72 that extends longitudinally through the handle portion 50, through the hollow catheter 70, and operatively connects to an inner volume of the balloon 60. Handle portion 50 includes a proximal leer lock 52 to removably engage hollow passage 72 with compressed gas and/or vacuum lines and or fluid lines, a valve 54 to control the flow of gas and vacuum to the distal balloon 60, a grip 56, and orientation wings 58. Hollow catheter 70 can be configured to have sufficient length to work with an endoscope 100 as described above, or long enough to work with a variety of endoscopes 100 with differing lengths.

Figure 3:
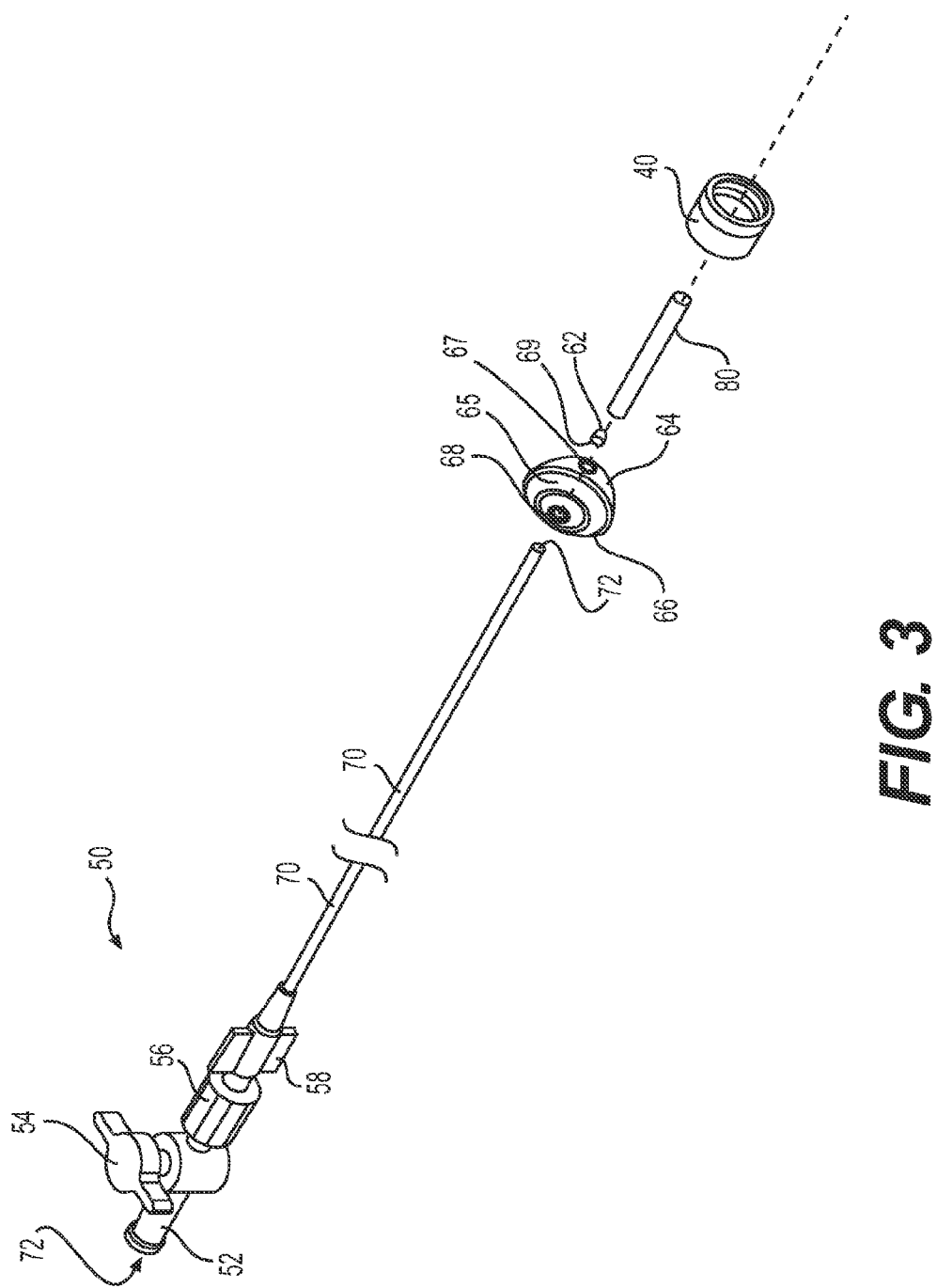
FIG. 3 is an isometric exploded view of the balloon access device
Figure 4:
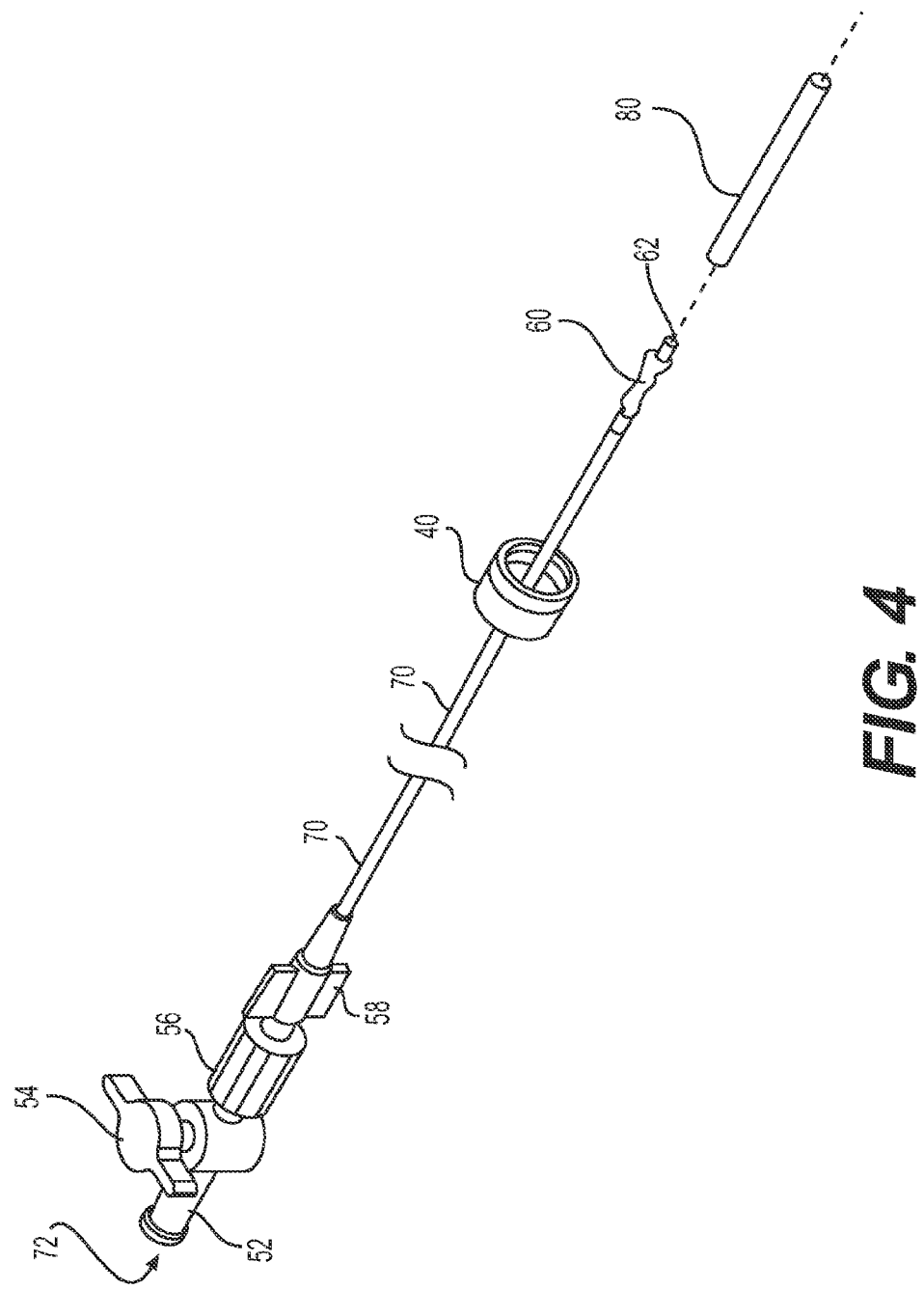
FIG. 4 is an isometric view of the balloon access device with the balloon shown collapsed by drawing a vacuum prior to being inserted into an adjacent balloon insertion tube.

In FIGS. 2 and 3, the transparent balloon 60 is shown in the normal unpressurized or "as manufactured" shape wherein the hollow balloon 60 can have a distal dome 64 and at least one sealing surface 66 on a proximal side. The balloon 60 is configured to be symmetrical and concentric about a longitudinal axis of the balloon 60 and a longitudinal axis of the catheter 70, and the distal dome 64 can be hemispherical or elliptical in shape about the axis. The balloon includes a proximal collar 63 which includes a proximal elongated projecting portion 68 and a base portion 66. The proximal collar 63 securely seals the balloon 60 to the catheter 70 via an attachment method such as but not limited thereto, by an adhesive or a shrink fit as described later. Elongated projecting portion 68 may have a shaped portion that is cylindrical, pyramidal, tapered, or bulbous, and can include a conical or curved portion for engaging with or sealing with the operative channel 102 of endoscope 100. The guide tip 62 can be a separate piece that can be secured to the dome of the balloon 60 in the exemplary manner. As best shown in FIG. 3, the guide tip 62 has a rounded distal tip and a stepped proximal post 69 that can be adhesively secured into a distal collar 67 formed from the balloon membrane 65. Alternately, the guide tip could be a rounded bump formed from the balloon membrane 65, or an injection of sealing material into the distal collar 67 such as a gob of silicone placed inside the distal collar 67. The guide tip 62 can be transparent for visualization therethrough, or can be opaque or translucent. As shown, guide tip 62 is supported by only the balloon membrane 65 which can provide some freedom of motion of the tip 62 relative to the endoscope 100. This freedom of motion can beneficial when navigating through collapsed tissue A hollow balloon insertion tube 80 is shown distal to the guide tip 62 may be provided to receive and store the balloon 60 and tip 62 within when the balloon is deflated by drawing a vacuum prior to being inserted into an adjacent balloon insertion tube 80, and tube 80 can have a length sufficient to guide the balloon 60 and tip 62 into and beyond a "Y" portion of the operative channel 102 within the endoscope 100. A deflated balloon 60 is shown in FIG. 4 just prior to insertion within a hollow of the balloon insertion tube 80. Before insertion, balloon 60 may have one or more deflation folds of the balloon 60 wrapped or twisted about a longitudinal axis of the balloon (not shown) to create a more compact and organized deflated balloon 60.

Figure 5:
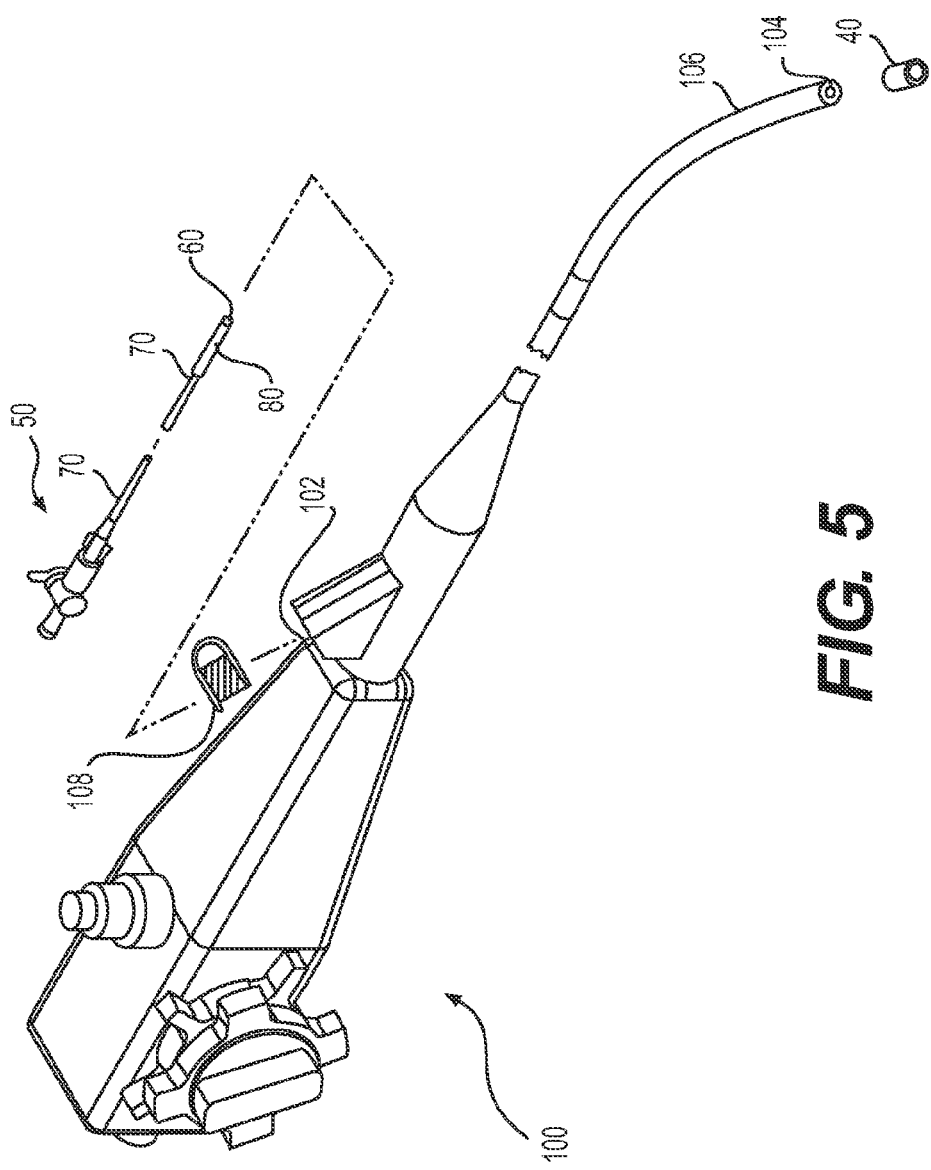
FIG. 5 is an isometric view of the balloon access device with a balloon seal cap placed on a distal end of the scope and with a dashed line illustrating a path where the balloon access device can enter an open instrument channel which exits within the attached balloon seal cap.

FIG. 5 shows the access device 30 ready for installation onto the endoscope 100. In this view, the cylindrical seal cap 40 is positioned for placement onto the distal end 106 of the endoscope 100. The balloon 60 is fully deflated as shown in FIG. 4, and resides within the balloon insertion tube 80. A dashed line is provided to show how the balloon insertion tube 80 of the access device 30 can be inserted into the proximal opening of the operative channel 102 of endoscope 100, and if a biopsy valve 108 is provided, through the biopsy valve 108. The balloon insertion tube 80 can be configured to feed the balloon 60 directly into the operative channel 102 through the balloon insertion tube 108 with the guide tip 62 leading the collapsed balloon. Balloon insertion tube 80 can be the length as shown, or can be longer to guide the collapsed balloon past a "Y" within operative channel 102 Balloon insertion tube 80 can be constructed from a slick or lubricious plastic such as PTFE, or can be lubricated to reduce egress of the collapsed balloon 60 into or out of the tube 80. FIG. 1 shows how the balloon insertion tube 80 can be retracted proximally around the catheter 70 to a position adjacent to the handle portion 50 after the full insertion of the access device 30 into the operative channel 102.

Figure 6:
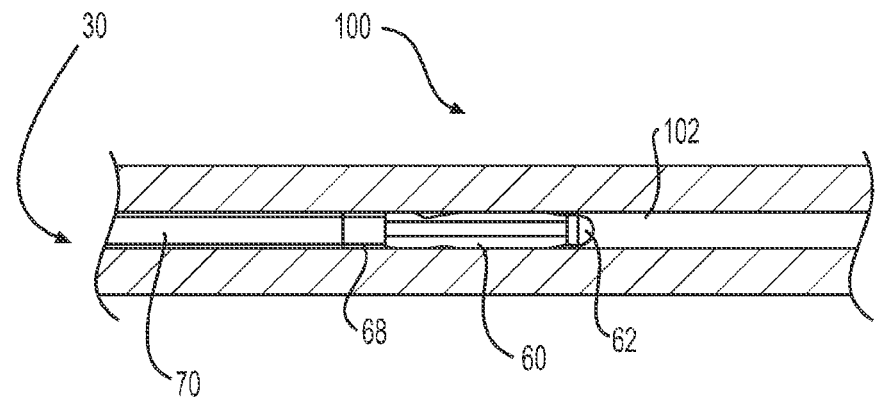
FIG. 6 is a side section view of the flexible shaft of the endoscope with an un-inflated balloon being pushed longitudinally along an instrument passage of the endoscope.

FIG. 6 shows the fully deflated balloon as it is being pushed down channel 102 of the endoscope 100 prior to emergence of the balloon 60 from the distal face 40 of the endoscope 100. The guide tip 62 can be configured with a tip diameter that is dose to the inner diameter of the operative channel 102 of the endoscope 100, and an appropriate length so that the tip 62 will not cock and jam within the operative channel 102 of the scope 100. The tip of the guide tip 62 can be any shape that is conducive to steering the guide tip along the operative channel 102 such as the rounded tip 62 shown, or any other guiding shape such as but not limited to a cone.

Figure 7:
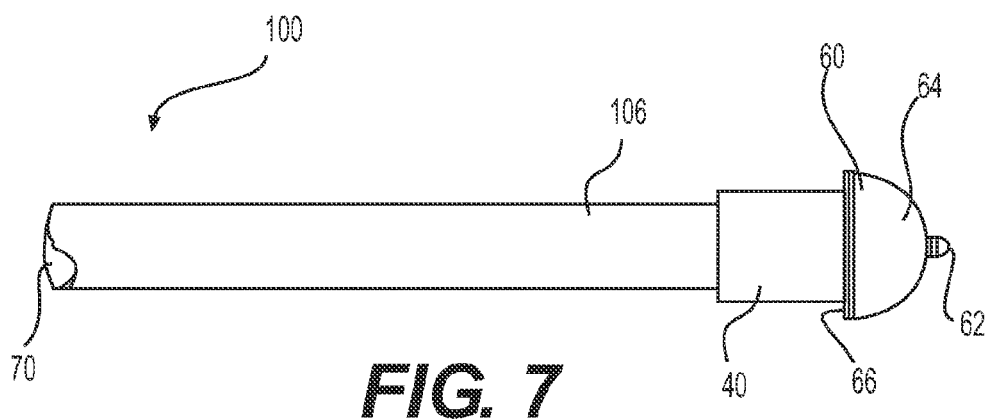
FIG. 7 is a side view showing the balloon after emerging from a distal end of the endoscope.

FIG. 7 shows the balloon 60 after emerging from the distal end 106 of the endoscope 100. Once the balloon 60 is extended from the endoscope 60 and beyond the seal cap 40, atmospheric air may be induced through the hollow passage 72 to allow the balloon 60 to expand into the non-pressurized shape as shown. Once the balloon 60 is fully inflated with a fluid, such as air, to an operating pressure or volume, the balloon 60 is pulled proximally in the direction of the arrow to engage the balloon 60 with the seal tip 40. This pulling of the balloon 60 to seal against the seal tip 40 can be accomplished by pulling on the catheter 70 or the handle portion 50 outside of the patient. If required, the balloon 60 is free to pivot somewhat about the attachment point to the catheter 70 to center itself in the seal cap 40.

Figure 8:
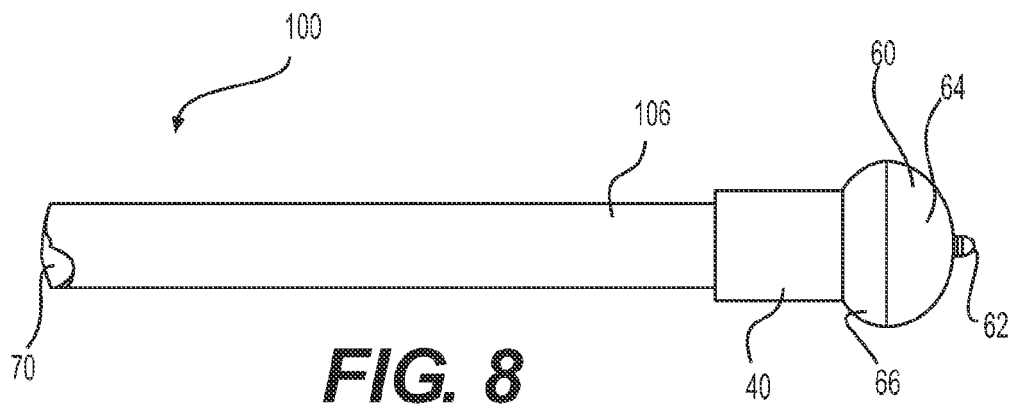
FIG. 8 is a side view showing the balloon inflated after emerging from a distal end of the endoscope.

FIG. 8 shows the fully inflated balloon 60 pulled against the seal cap 40 at the distal end 106 of the endoscope 100. In this view, it can be seen that the inflation of the balloon 60 has changed the at least one base portion 66 of proximal collar 63 into a rounded dome that has maintained a fluid-tight seal with the seal cap 40. The rounding of the at least one base portion 66 has moved the distal dome 64 distally, and the distal dome 64 has expanded both in diameter and longitudinally as shown. The inflation of the balloon 60 can be accomplished prior to insertion of the endoscope 100 into the patient, or after insertion of the endoscope 100 into the natural orifice such as the anus of the patient.

FIGS. 9 through 12 shows exploded cross sectional views of alternate exemplary embodiments of the balloon 60, and balloon seal cap 40 of the present apparatus. The guide tip 62 is also depicted. The exemplary and previously described embodiment of balloon 60 and seal cap 40 is best shown in FIGS. 2, and 3, and is shown in cross section in FIG. 11. The reader is advised to note that the balloon access device 30 is not limited to the previously described embodiment of FIG. 11, nor to the alternate embodiments of FIGS. 9-10 and 12, nor to any of the materials or manufacturing techniques described. Since many of the embodiments of the balloons and seal caps have features that perform the same function, like numbers are identified with sub-identifiers and are meant to correspond to like features on alternate embodiments. For example, a balloon 60 in one embodiment may become a balloon 60a in another alternate embodiment. If differences in functions exist between like numbers such as base portions 66 and 66a, the description associated with the number and sub-identifier will prevail for that embodiment. All embodiments described below have a balloon 60, 60a, 60b, 60c and a seal cap 40, 40a, 40b, 40c.

Figure 11:
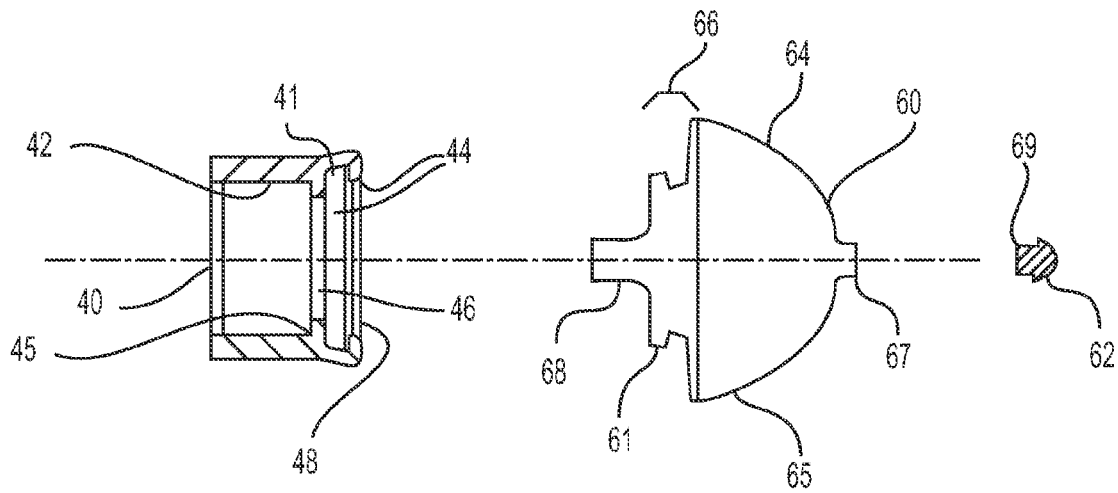
FIG. 11 shows an exploded cross sectional view of an embodiment of the balloon and balloon seal cap.

The embodiment of FIG. 11 comprises the hollow balloon 60, the balloon seal cap 40 and the guide tip 62. This embodiment uses a ring-in-groove seal between the balloon and seal cap 40. The balloon 60 comprises the previously described distal dome 64, the membrane 65, and the at least one base portion 66 of the proximal collar 63. With this embodiment of the balloon 60, the at least one base portion 66 of the balloon comprises two distinct portions. The first portion comprises a circular rib 61 that rings the longitudinal axis of the balloon 60 and is configured to engage with and seal with the circular groove 41 in the seal cap 40. The second portion of the at least one base portion 66 is a dish shaped portion that extends substantially radially inwardly between the largest diameter of distal dome 64 to the circular rib portion. The dish shaped portion can be configured to seal against at least a distalmost surface 48 of the cap 40. The distal collar 67 of balloon 60 extends distally from the dome 64 and is configured to seal with the distal tip 62. The elongated projecting portion 68 of the proximal collar extends proximally from the at least one base portion 66 and is configured to seal with the hollow catheter 70 (see FIGS. 2 and 3).

The balloon seal cap 40 of FIG. 11 comprises a hollow cylinder having an endoscope receptacle 42 extending into a proximal end of the seal cap 40 to receive and seal with the distal end 106 of the endoscope 100. A circular rib 45 can be provided at a distal end of the endoscope receptacle 42 to act as a stop that engages the front face 104 of the endoscope 100 once the scope 100 is fully received within the seal cap 40. An opening 46 is provided through the rib 45 to distally expose the optics, lights, and openings on the endoscope front face 104. A balloon sealing portion 44 extends distally from the rib 45 and includes the previously described circular groove 41 to retain and seal with the circular rib 61 of the balloon 60. The distalmost surface 48 of the balloon sealing portion 44 can seal with the balloon 60. As shown, the receptacle 42, the opening 46, and the balloon sealing portion 44 comprise the open hollow of the cylindrical seal cap 40.

Figure 9:
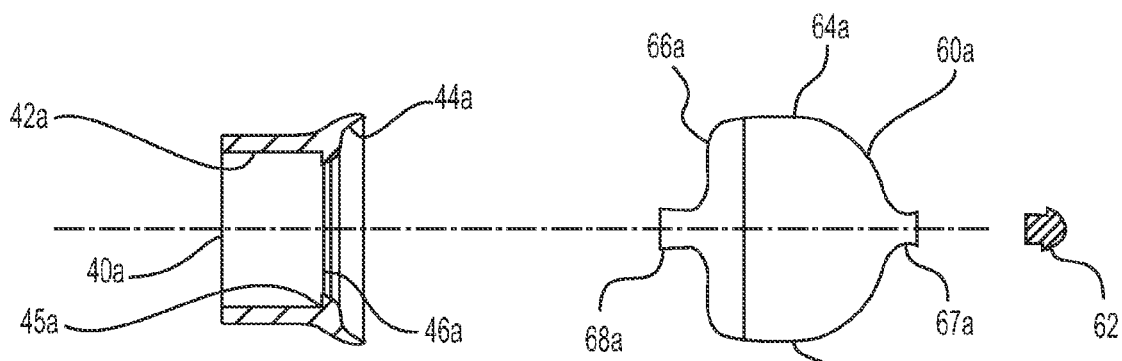
FIG. 9 shows an exploded cross sectional view of an embodiment of the balloon and balloon seal cap.

The embodiment of FIG. 9 comprises a balloon 60a and a seal cap 40a and is configured to provide a ball-in-socket type of sealing. The balloon 60a has a substantially curved base portion 66a that nests within and seals with an outwardly flaring cuplike baboon sealing portion 44a of the seal cap 40a. Seal cap 40a can be configured to flare outward to provide a larger support for the balloon 60a and can exceed the diameter of the endoscope 100. Seal cap 40a is a hollow cylinder that further comprises an endoscope sealing receptacle 42a, circular rib 45a, opening 46a, as well as the previously described balloon sealing portion 44a. Balloon 60a includes a distal dome 64a, a membrane 65a, a distal collar 67a, and a proximal elongated projecting portion 68a. Cuplike balloon sealing portion 4a of the seal cap 40a can also be used to flatten luminal folds, for example to discern pathologies behind the luminal folds.

Figure 10:
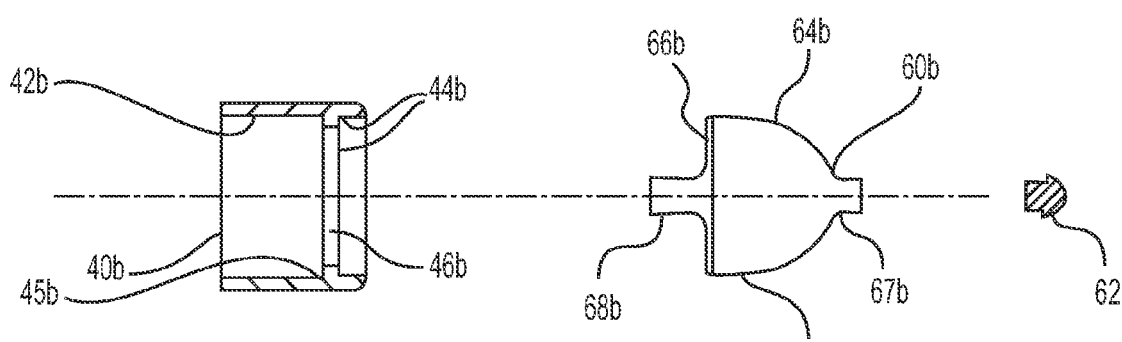
FIG. 10 shows an exploded cross sectional view of an embodiment of the balloon and balloon seal cap.

The embodiment of FIG. 10 comprises a balloon 60b and a seal cap 40h and uses a peg-in-hole arrangement for sealing. In this embodiment, the balloon 60b is sized to have about the same radial diameter as the distal end 106 of the endoscope and the balloon 60b nests and seals with a receptacle of a cylindrical balloon sealing portion 44a. Mushroom shaped balloon 60a comprises a distal dome 64 with at least one base portion 66a that is substantially flat and circular. Balloon 6b is configured to fit snugly in the cylindrical balloon sealing portion 44a and to seal the at least one sealing surface 66a against a rib 45b. Cylindrically shaped cap 40b further comprises an endoscope sealing receptacle 42b, and an opening 46b extending through rib 45b. Balloon 60b includes a distal dome 64b, a membrane 65b, a distal collar 67b, and an elongated projecting portion 68b.

Figure 12:
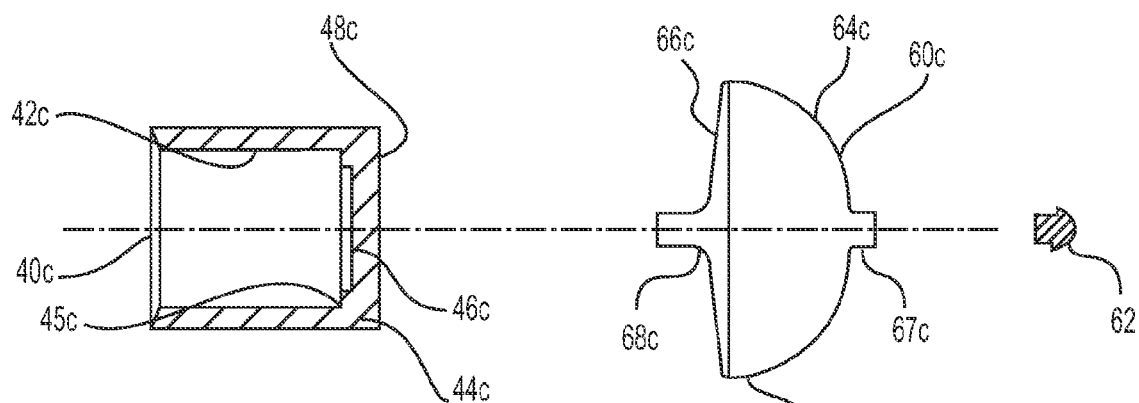
FIG. 12 shows an exploded cross sectional view of an embodiment of the balloon and balloon seal cap.

The embodiment of FIG. 12 comprises a balloon 60c and seal cap 40c that is configured to provide a flat-to-flat seal as the balloon 60c is pulled against a distalmost surface 48c of seal cap 40c. As the inflating balloon 60c changes shape from the mushroom shape to a rounded elliptical ball shape, the seal can move to a beveled portion of a distal balloon sealing portion 44c. Balloon 60c may be substantially mushroom shaped with a substantially flat at least one sealing surface 66c adjacent to a dome 64c. Unlike the embodiment of FIG. 10, the balloon 60c is larger than an outer diameter of a seal cap 40c and overhangs the seal cap 40c. Cylindrically shaped cap 40c further comprises an endoscope sealing receptacle 42c, circular rib 45c, and opening 46c. Balloon 60a further comprises a distal dome 64a, a membrane 65a, a distal collar 67a, and an elongated proximal projecting portion 68a.

The balloons 60, 60a, 60b, and 60c are transparent and can be constructed from a substantially rigid balloon material or an elastomeric material.

Substantially rigid materials cannot expand greatly beyond the normal "as made" shape when inflated and many such materials are well known in the art for use as expansion balloons for cardiac stent deployment products. Elastomeric balloons are expandable, and can comprise material such as, for example, some grades or durometers of elastomers such as polyurethane, latex, natural rubbers, silicones and the like.

The seal caps 40, 40a, 40b, and 40c can comprise a substantially rigid material such as a thermoform plastic, a thermoset plastic, or a metal. With rigid embodiments of the caps, it is the deformation of the balloon 60, 60a, 60b, and 60c against the rigid cap that creates the seal. In yet another embodiment, the seal caps 40, 40a, 40b, and 40c can comprise an elastomeric material such as but not limited to a polyurethane, a polyethylene, silicone, rubber and the like. As such, the elastomeric properties of this embodiment can have sufficient rigidity to generally support the balloon against normal surgical operating forces, yet provide atraumatic characteristics, should substantial resistance be encountered. Rigidity of the elastomeric material could be altered by changing a clinometer of the material during manufacturing.

Alternately, the distal balloon sealing portion 44, 44a, 44b, 44c of the caps 40, 40a, 40b, and 40c could be rigid or elastomeric and can further comprise one or more deformable gasket materials to create a seal such as but not limited to: an elastomeric lip seal, an o-ring, an over-molded elastomer, or a foam seal (not shown). Such seals can seal with the balloon 40, the endoscope 100 or both.

The distal guide tip 62 can be used with any balloon embodiments such as 60, 60a, 60b, and 60c. The distal guide tip 62 can include the stepped proximal post 69 which is configured to fit within the distal collar 67, 67a, 67b, or 67c to create a smooth exterior when mated with the balloon 60, 60a, 60b, or 60c (see at least FIGS. 1 & 2). The guide tip 62 and catheter 70 can be adhered to the balloon 60, 60a, 60b, or 60c with adhesives such as but not limited to polyurethanes or cyanoacrylates. Or, alternate fastening techniques can be used with distal guide tip 62 and catheter 70 such as but not limited to heat staking, ultrasonically welding, or laser welding. Whereas these fastening techniques are described for the attachment of the distal guide tip 62, they can be used for all other embodiments of the apparatus such as elements of the handle portion 50 or attachment of the proximal collar 63 to the catheter 80.

FIGS. 13-16 are side views that detail the inflation of the distal portion of the balloon access device 30 on the endoscope 30. The mushroom shaped balloon 60c and cap 40c are the embodiments shown in cross section in FIG. 12. For this inflation description, only the embodiment of FIG. 12 will be described, and the description is based on physical measurements of an actual balloon 60c and cap 40c as the balloon 60c is inflated.

Figure 13:
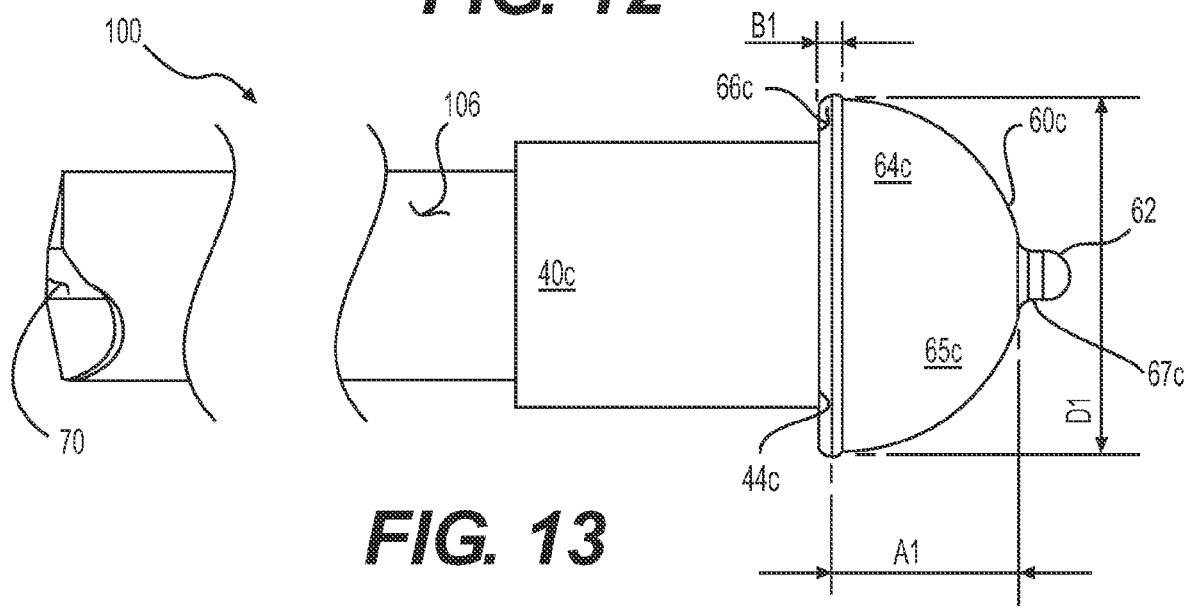
FIG. 13 shows the balloon of FIG. 12 in a normal un-inflated shape wherein the inner air pressure is the same as the outside atmospheric pressure.

FIG. 13 shows balloon 60c in a normal un-inflated normal shape wherein the inner air pressure is the same as the outside atmospheric pressure and the balloon 60c has assumed the "as manufactured" mushroom shape. As shown, the normal shape of balloon 60c is substantially mushroom shaped, and comprises the distal dome 64c attached to the proximal at least one base portion 66c. The at least one base portion 66c is substantially flat and has been pulled back (via catheter 70) to seal against a ring of contact with the ring shaped distalmost surface 48c of the seal cap 40. With atmospheric pressure within balloon 60c, and the valve 54 of the handle portion 50 closed, the balloon 62 is very flaccid and the guide tip 62 is substantially supported by only the membrane 65c. Pushing the guide tip 62 towards the catheter 70 creates a large indention crater with the tip 62 standing proud within as the tip 62 is completely pushed into the dome 64c. Measurements of the balloon 60c of FIG. 13 show an outer dimension D1 of about 18 mm at the widest diameter, and the sum of longitudinal lengths A1 and B1 equal about 11 mm. The balloon 60c and catheter 70 of the actual test balloon 60c required about 2-2.1 ml of air to arrive at the flaccid shape of FIG. 13.

Figure 14:
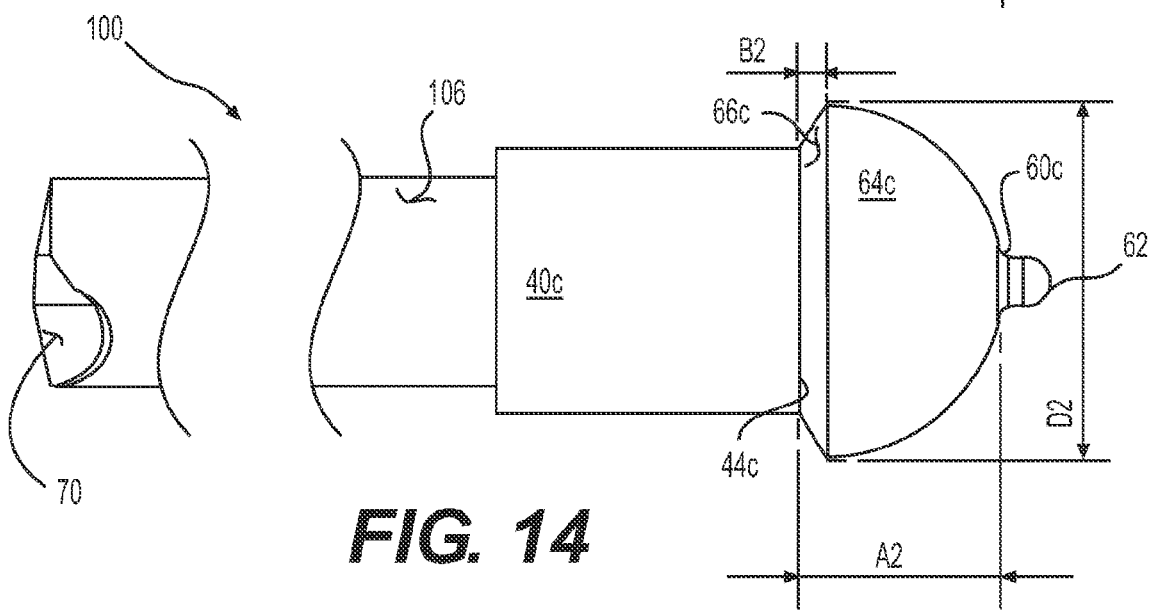
FIG. 14 shows the balloon of FIG. 12 in an inflated shape where about 2.5 ml of air have been placed into the balloon and cannula.

FIG. 14 is another side view of the access device 30 on the endoscope 100 where about 2.5 ml of air have been placed into the balloon 60c and catheter 70. At this air volume, the distal dome 64c maintained substantially the same shape, but the at least one base portion 66c domed slightly and pushed the distal dome 64c and guide tip 62 in the distal direction. This increased the sum of longitudinal lengths A2 and B2 to about 11.7 mm without an appreciable change in D2. It is visually seen that the majority of the 0.7 mm balloon longitudinal length change occurred in the doming of the at least one base portion 66c which increased dimension B2. Pushing on the distal guide tip 62 so that it is embedded within the balloon created a slightly smaller dish shaped indent with the guide tip 62 standing proud in the indent. The increased volume of fill also increased the resistance to movement of the tip 62. The balloon 60c did not appear to move longitudinally from pushing on the guide tip 62 but expanded radially when filled with 2.5 ml of air.

Figure 15:
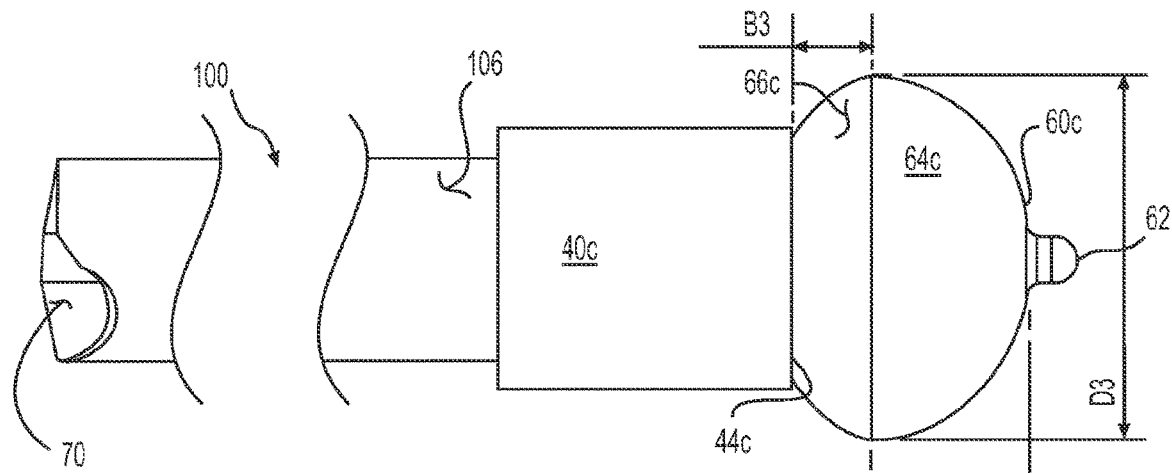
FIG. 15 shows the balloon of FIG. 12 in an inflated shape where about 3.5 ml of air have been placed into the balloon and cannula.

FIG. 15 is another side view of the access device 30 on the endoscope 100 where about 3.5 ml of air have been placed into the balloon 60c and catheter 70. Once again, the distal dome 64c maintained substantially the same shape and the at least one base portion 66c continued to move towards a dome shape. The longitudinal length (sum of A3 and B3) increased to about 12.2 mm with the majority of the 0.5 mm additional length increase coming from additional doming of the at least one base portion 66c. The dimension D3 increased slightly to 18.73 mm. When the guide tip 62 was pushed distally into the balloon 60c, the distal guide tip 62 had substantial resistance. Pushing on the distal guide tip 62 so that it is embedded within the balloon created a noticeably smaller dish shaped indent with the guide tip 62 standing proud in the indent. As the guide tip 62 was embedded into the balloon 60c, the balloon 60c also moved distally as some of the distal movement of the guide tip 62 was transferred to the balloon 60c. Visually, it appears that there is about the same amount of distal longitudinal movement of the balloon 60c as there is distal embedding of the guide tip 62. The distal movement of the balloon 60c is primarily in the at least one base portion 66c.

Figure 16:
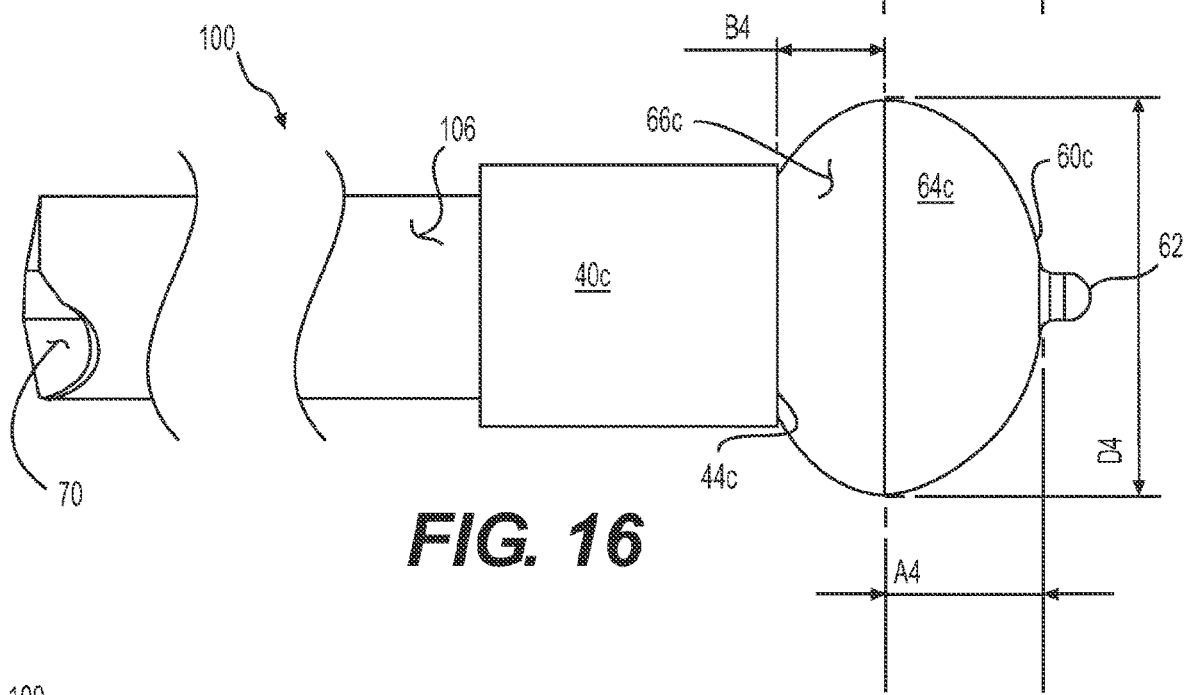
FIG. 16 shows the balloon of FIG. 12 in an inflated shape where about 5 ml of air have been placed into the balloon and cannula.

FIG. 16 is another side view of the access device 30 on the endoscope 100 where about 5 ml of air have been placed into the balloon 60c and catheter 70. The diameter D4 reduced back to the original 18 mm diameter and the longitudinal length (sum of A4 and B4) increased to about 14.75 mm. Once again, the majority of the additional length increase (2.55 mm) appears to be coming from additional doming of the at least one base portion 66c. There was some additional rounding of the distal dome 64c which may account for some of the reduction in overall diameter D4 and some of the length change. With respect to pushing distally on the guide tip 62 with 5 ml of air, the guide tip 62 has substantial resistance and the combination of balloon geometry (mushroom shape), fill volume (ml) balloon membrane 65c thickness and material durometer have combined to provide an unexpected shift in load transfer that seems to prevent the guide tip 62 from creating much of a dish indent in the balloon. With this fill volume, a substantial portion of the movement of the guide tip 62 towards the catheter 70 comes from a longitudinal compression of the balloon 60c to a different elliptical shape, and not from dishing the guide tip 62 into the balloon 60. This effect may be advantageous to tunneling through non-insufflated tissue lumens to maintain the distalmost positioning of the guide tip 62 during airless burrowing of the access device 30 and the endoscope 100. It is the distalmost position of the guide tip 62 which can enable the guide tip 62 to initiate separation of the collapsed luminal tissue. Once the initial separation occurs, the collapsed tissue separation may then be transferred to the outer surface of the balloon 60c as the access device 30 and endoscope 100 advances along the GI tract.

Figure 17:
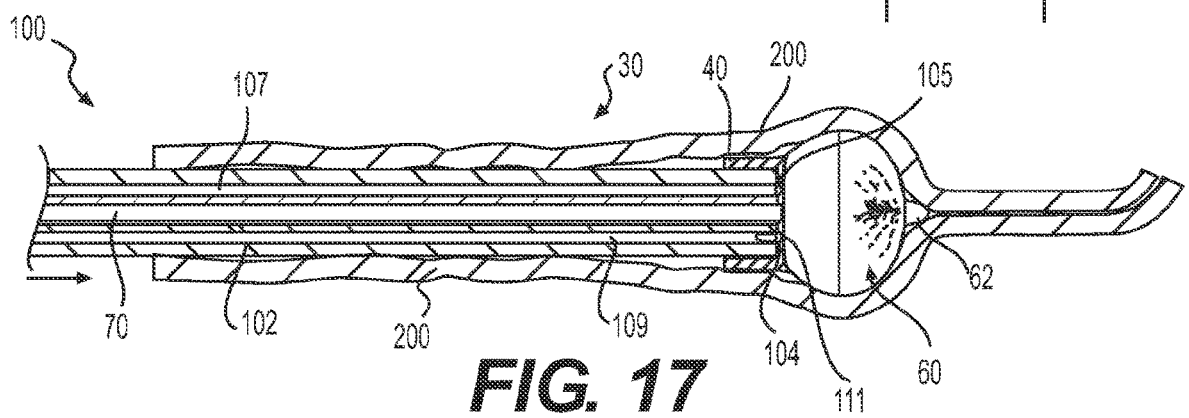
FIG. 17 is a side cross sectional view of the balloon access device installed upon an endoscope as the balloon access device spreads tissue to burrow through non-insufflated and collapsed luminal tissue.
Figure 18:
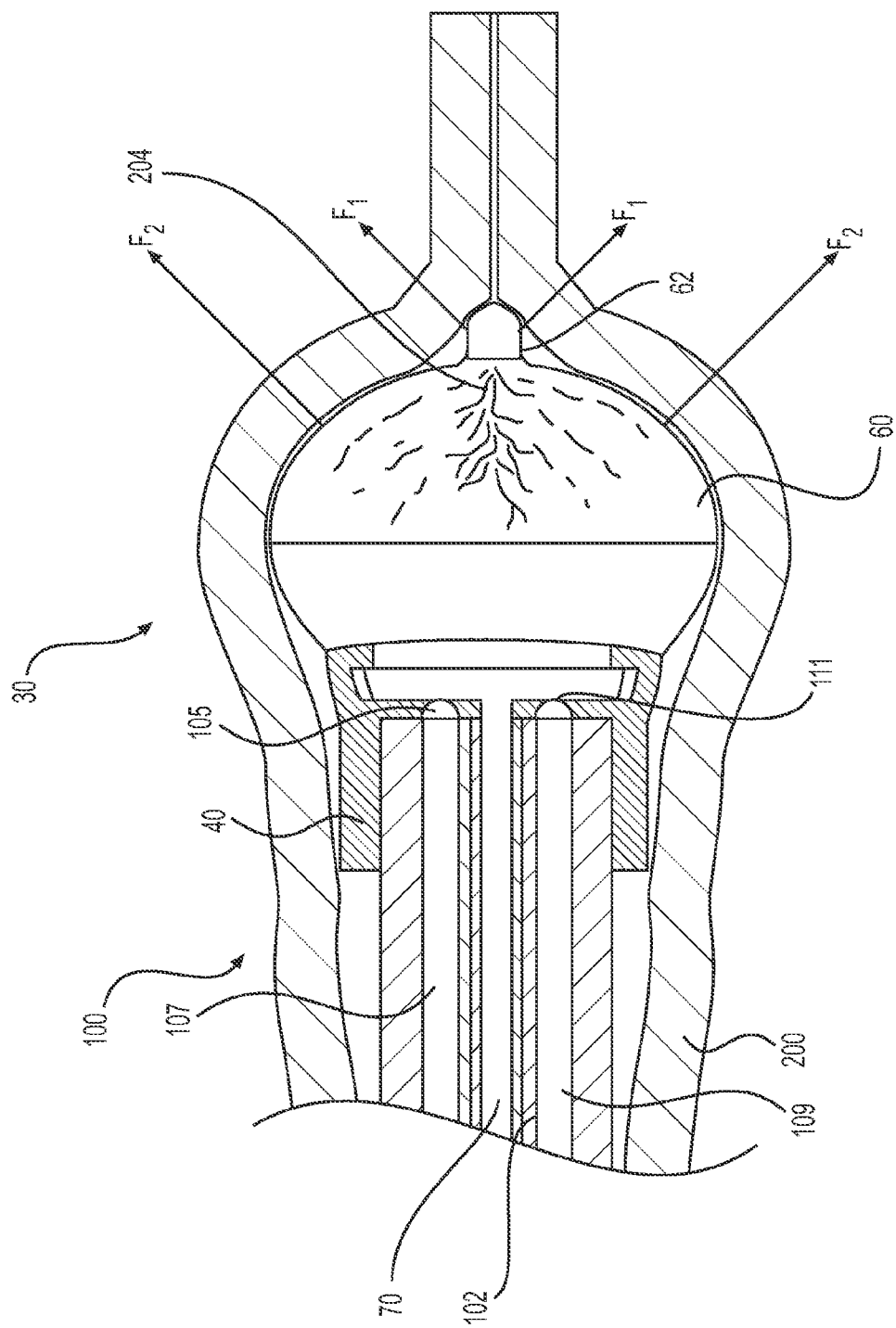
FIG. 18 is an enlarged side cross sectional view of the balloon access device of FIG. 17 showing spreading forces on the collapsed luminal tissue.

FIGS. 17 and 18 are side cross sectional views of the balloon access device 30 installed upon an endoscope 100 as it burrows through non-insufflated luminal tissue of the GI tract. FIG. 18 is an enlarged view of a portion of the cross sectional view of FIG. 17. As shown, the luminal tissue has collapsed, and the balloon access device 30 is providing both a visualization pocket and a tissue separator for the operator of the endoscope 100 so that the endoscope 100 can be easily advanced farther into the patient. An arrow is provided to indicate the direction of movement of the balloon access device 30 and endoscope 100. In this cross section, the collapsed luminal tissue 200 is partially spread by the balloon access device 30 and endoscope 100 as it burrows towards a bend in the tissue 200. The endoscope 100 is shown in cross section and has the operative channel 102 and front face 104 shown. Front face 104 of the scope 100 further comprises a lens 105 that views tissue through the transparent balloon 60. A visualization channel 107 may extend through the shaft of the endoscope for relaying images to the user. An illumination channel 109 and light 111 may also be included on these or other embodiments to assist in visualization of the intestinal wall.

A viewing angle of the lens 105 is shown as dashed lines extending from the lens 105 (see FIG. 18). To prevent reduction of the viewing angle, the cap 40 may protrude above the front face 104 of the scope between about 0.5 mm to about 6 mm. Alternately, the cap 40 may protrude above the front face 104 of the scope between about 1 mm to about 3 mm. If desired, the vacuum in the endoscope 100 can be used to draw the balloon 100 against the front face 104 and the lens 105 of the endoscope 100. The hollow catheter 70 extends longitudinally along the operative channel 102 and is attached to the balloon 60 which is inflated (via the catheter 70) art amount that substantially restricts the embedding of the guide tip 62 into the balloon as described previously. The cap 40 is sealed against the endoscope and the balloon 60 is sealed within the cap 40 to seal the front face 104 of the endoscope 100 from fluids, mucous, and residual natural materials normally found within the luminal structure. As shown, ring 61 of the balloon is embedded in the groove 41 in the seal cap 40 to create a seal.

FIG. 18 is an enlarged side cross sectional view of FIG. 17. In this view, the spreading of the collapsed opening 204 of the tissue 200 can be seen through the transparent balloon 60. The lens 105 of the endoscope can be seen with dashed lines indicating a field of view through the balloon access device 30. Arrows show how a spreading force F1 is applied from the guide tip 62 onto the tissue 200. The guide force F1 is perpendicular or normal to the point of contact on the tissue. A second spreading force F2 is exerted on the tissue by the inflated balloon 60. Once again, the spreading force F2 is perpendicular or normal to the point of contact of the membrane 65 of the balloon 60 on the tissue.

Figure 19:
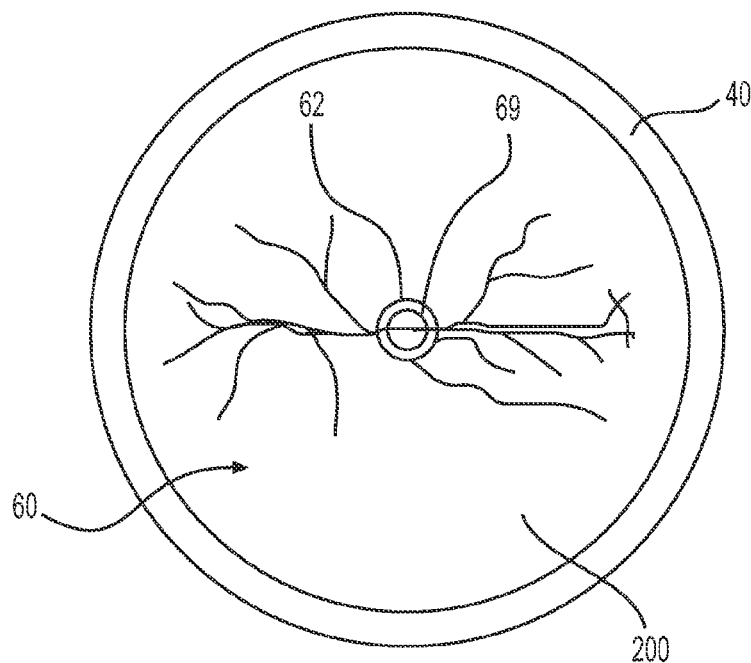
FIG. 19 is a view through the camera lens of the endoscope showing a guide tip of the balloon moved to a centered position in a collapsed tissue lumen opening to ensure passage of the balloon and endoscope down a center of the lumen.

FIG. 19 is a view through the lens 105 of the camera of the endoscope 100 looking at collapsed tissue through the transparent balloon 60 and guide tip 62. In this view, the surgeon has steered the guide tip 62 of the balloon 60 to a centered position of the collapsed tissue opening 204 of the tissue 200. Since the tissue guide 200 is transparent, tissue 200 can be seen therethrough. Once the guide tip 62 of the balloon 60 is centered, the surgeon is confident that the balloon access device 30 and endoscope 100 are aimed at the center of the collapsed lumen, and that the balloon access device 30 and endoscope 100 can now be pushed down a center of the lumen such as the large intestine. During testing of the device in actual tissue, several of the medical professional operators were surprised at the depth of penetration of the balloon access device 30 equipped endoscope 100 in such a short time.

Figure 20:
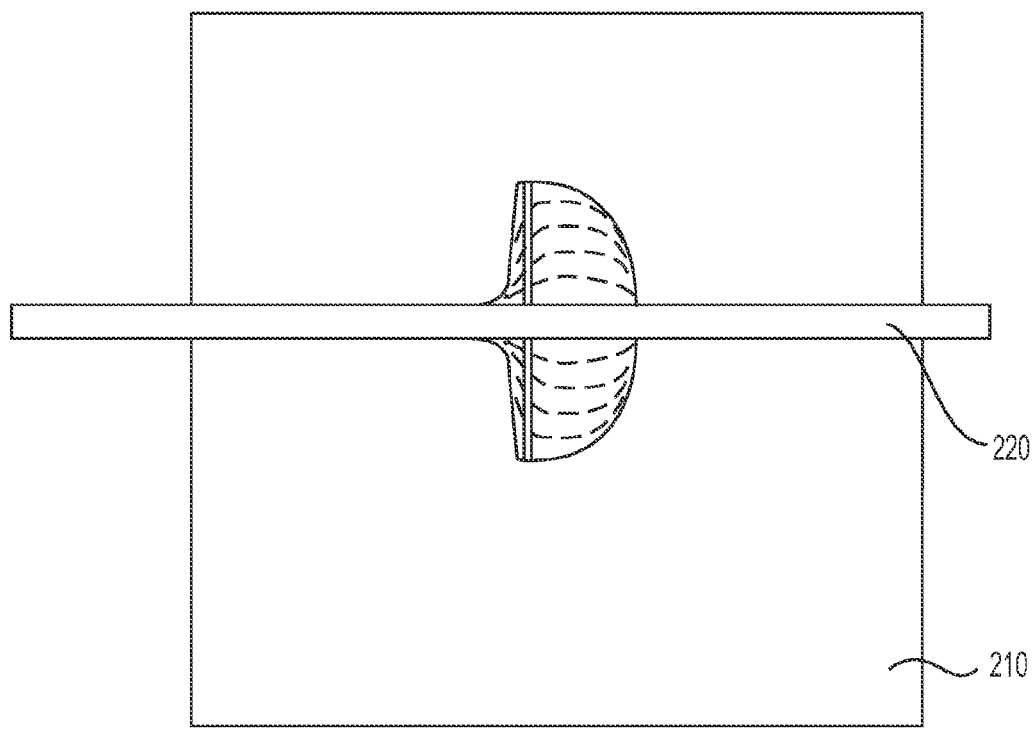
FIG. 20 is a cross sectional view of a blow molding dies that is configured to make the balloon of FIG. 12.

FIG. 20 is a cross sectional view of a blow molding dies that is configured to make the balloon of FIG. 12. As shown, the blow molding die 210 has a piece of expandable polyethylene tubing 220 placed along a longitudinal axis of the balloon shape of the die 210. Once the tubing 220 is heated, warm compressed air can be blown to expand the polyethylene tubing 220 against the cooler inner walls of the mold 210 which can be held slightly below the melting temperature of the polyethylene tubing 220. When the flow of warm expansion air is shut off, the tubing 220 has expanded against the walls of the mold 210 and sets in the net or normal "as manufactured" shape. Then the molded balloon 60 can be extracted by opening the die 210 to release the balloon 60. The dashed lines show the expansion stages of the polyethylene tubing 220 as it expands towards the mold walls 210. The natural tendency of the hot tubing 220 is to expand as a sphere until the expanding material contacts the walls of the die 210. As a consequence, different portions of the balloon membrane 65 (see FIG. 2) will be thinner than others and may taper between the thick and thin portions. For example, the portions of the tubing 220 that form the elongated projecting portion 68 and distal collar 67 will expand not at all or very slightly and will be thicker than the balloon membrane 65 at the points of largest expansion away from the longitudinal axis. The shape of the balloon can affect the location of the thick and thin membrane 65 portions and a stiffened disk may be found near the elongated projecting portion 68 and distal collars 67, which can affect the manner in which the balloon 60 expands (see FIGS. 13-16). This thickening could affect or restrict the displacement of the guide tip 62 from tissue contact by creating a more rigid "island" of membrane 65 around the distal tip 62 that may explain the deflection behavior described previously. In an alternate embodiment, the balloon 60 can be further stiffened in local areas by a dipping process to build up the balloon wall thickness. For example, the same material as the balloon membrane 65 can be used (such as polyurethane), or alternate dipping material may be used.

Figure 21:
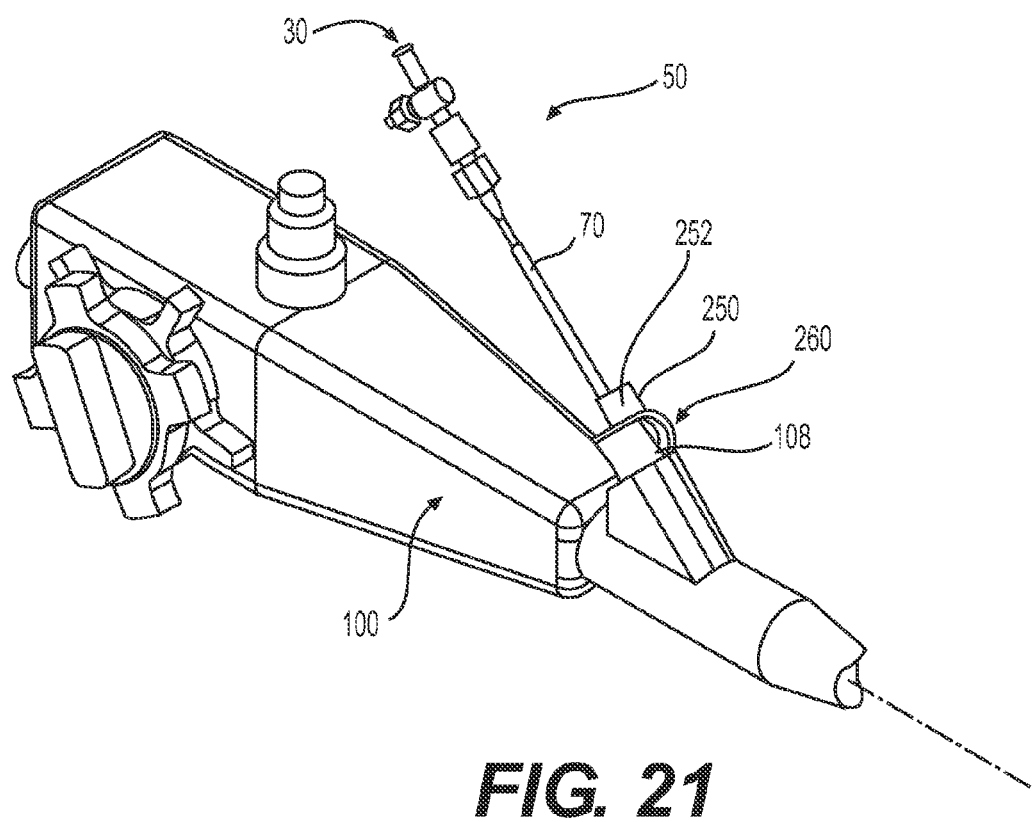
FIG. 21 is an isometric view of a clamp mechanism to clamp or lock the tensioned cannula relative to the endoscope to maintain a sealing contact between balloon and seal cap.

With some embodiments of the balloon such as that found in FIG. 12, a tension or pulling force may be applied to the catheter 70 to pull the balloon 60c into contact with the seal cap 40c to create a seal. It may be further desirable to include a lock or clamp mechanism 250 to hold the catheter 70 relative to the endoscope to ensure that the fluid tight seal is maintained in all tissue contacting situations. FIG. 21 illustrates an embodiment of a clamp mechanism 250 that can be used to clamp or lock the tensioned catheter 70 relative to the endoscope 100 to maintain a sealing contact between balloon 60c and seal cap 40c. Clamp mechanism 250 comprises a releasably lockable clamp mechanism that contacts and grips catheter 70 and is actuated and released via a pull member 252 to clamp the catheter 70. Alternate clamp mechanisms such as clamp mechanism 260 can surround the catheter 70 and retain it in place via frictional contact. One example of clamp member 260 would be a biopsy valve 108 or an adaption thereof wherein the biopsy valve 108 grips the endoscope 100 and the catheter 70 with an elastomeric material. And, in yet another embodiment of a clamp mechanism, the proximal balloon collar 63 may be configured to expand within the operative channel 102 of the endoscope 100 to lock the inflated balloon to the end of the endoscope. When the balloon is deflated, the proximal collar 63 unlocks from the operative channel 102.

Figure 22:
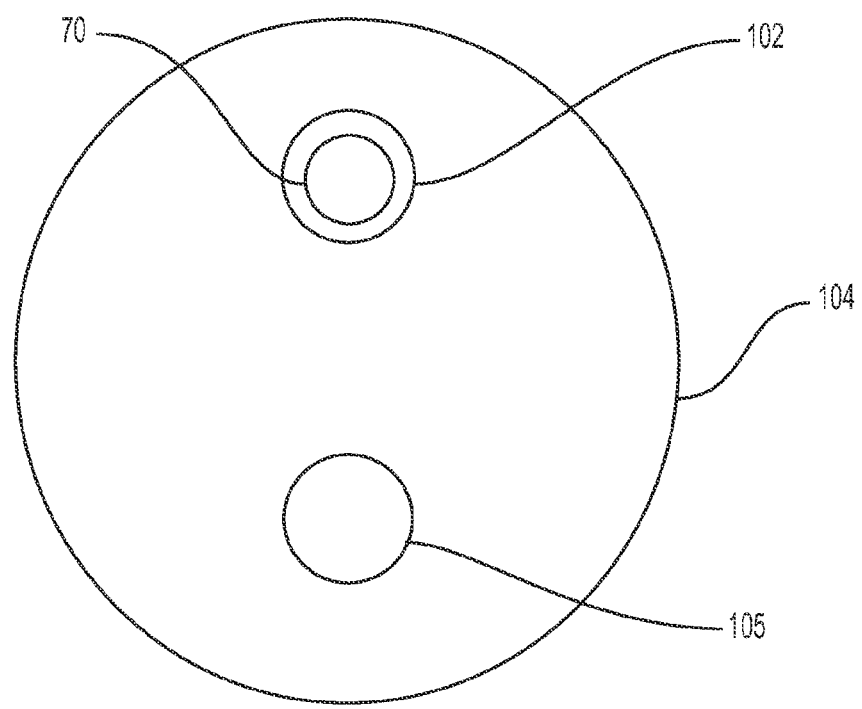
FIG. 22 is a front view of a distal end of an endoscope.

Turning now to FIG. 22, a front view of the front face 104 of the endoscope is shown. The operative channel 102 of the endoscope is non-concentrically disposed in the endoscope, and accordingly the catheter 70 and balloon are non-concentrically disposed relative to a central axis of the endoscope. As described previously, when the cap 40 and balloon 60 are installed on the endoscope, pulling on the catheter seals the balloon 60 against the cap 40 and the non-concentrically disposed balloon 60 is free to pivot somewhat about the attachment point to the catheter 70 to center itself in the seal cap 40.

During operation, as the balloon 60 pushes tangentially against the intestinal wall, the force attempts to unseat the balloon from the cap. The flaring portions of the cap, shown in FIG. 9 for example, seat the balloon to prevent the seal between the balloon and the cap from being broken or otherwise compromised. Additionally or alternatively, the cap, for example the cap shown in FIGS. 9-12, may include one or more longitudinal cuts in a portion of the cap protruding past the distal end 106 of the endoscope to prevent the balloon from being unseated from the cap when the balloon pushes against the intestinal wall. Alternatively, the portion of the cap protruding past the distal end 106 of the endoscope may have portions of varying heights to seal with the balloon.

FIGS. 23-29 depict balloon and endoscope embodiments that are configured for use with or without cap 40. These balloon embodiments may optionally have, the same or similar dimensions as balloon 60c of FIGS. 13-16. As demonstrated in the cross sections of FIGS. 23A-C, the balloons 60d, 60e, and 60f may be positioned such that the elongated projecting portion 68 of proximal collar 63 inflates to contact the operative channel 102 of the endoscope. After at least partial inflation, the user may pull back on the catheter 70 to bring the base portion 66 of proximal collar 63 into contact with the lens 105 (over the visualization channel 107). The transparent nature of the balloon allows for the visualization of the intestinal surfaces through both the proximal and distal ends of the balloon 60d, 60e, or 60f. Inflation of the proximal projecting portion 68 against the wall of the operative channel 102 stabilizes the balloon to prevent it from sliding off the lens 105. This improves the clarity of the image that is transmitted to the user though visualization channel 107 by preventing fluids from reaching the lens 105. An illumination channel 109 and light 111 may also be included on these or other embodiments to assist in visualization of the intestinal wall. The illumination channel and light may be covered by the base portion 66 of the balloon in its partially or fully inflated state, such that the light is directed through the base portion and the distal dome 64 to illuminate the intestinal wall. In FIGS. 23A-C, the operative channel 102 is positioned around the longitudinal center of the endoscope 100. However, other embodiments may include an operative channel that is off-center as shown in FIG. 22.

Figure 23A:
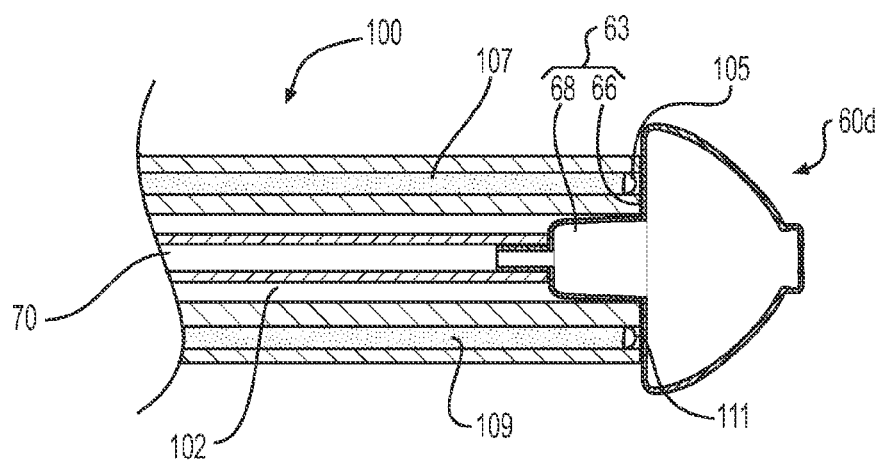
FIG. 23A is a side section of an endoscope with an inflated balloon.
Figure 23B:
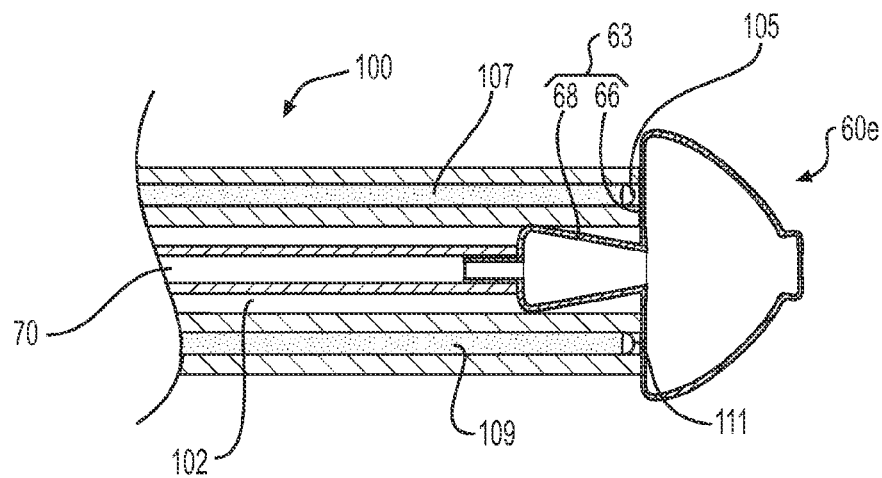
FIG. 23B is a side section of an endoscope with another embodiment of an inflated balloon.
Figure 23C:
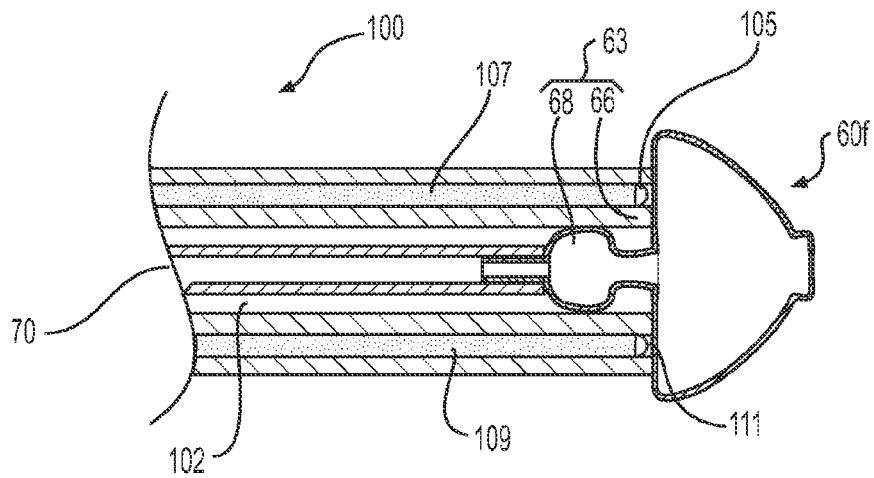
FIG. 23C is a side section of an endoscope with another embodiment of an inflated balloon.
Figure 24:
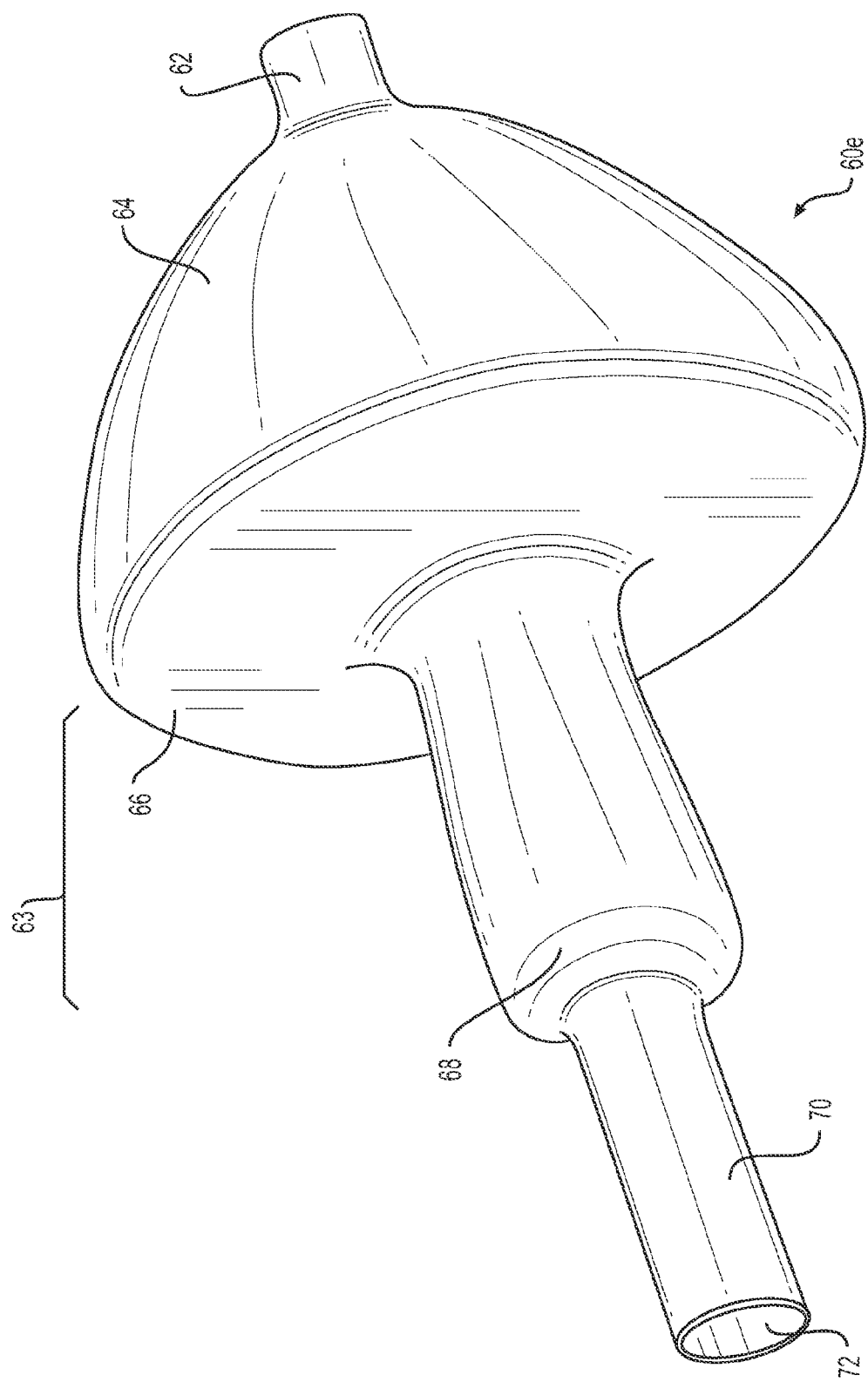
FIG. 24 is a perspective view of a balloon.
Figure 25A:
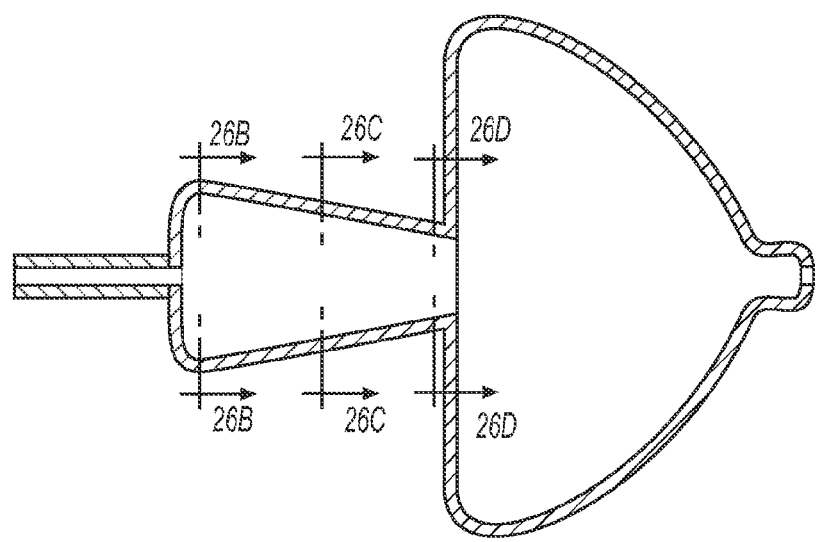
FIG. 25A is a side section of a balloon.
Figure 25B:
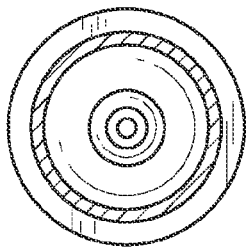
FIG. 25B is a transverse section of a balloon along the section line designated in FIG. 25A.
Figure 25C:
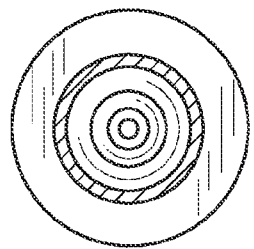
FIG. 25C is a transverse section of a balloon along the section line designated in FIG. 25A.
Figure 25D:
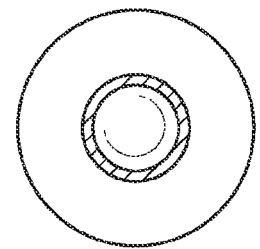
FIG. 25D is a transverse section of a balloon along the section line designated in FIG. 25A.

As seen in FIGS. 23A-C, the proximal collar 63 may take different shapes. For example, balloon 60d of FIG. 23A may have a collar with a shaped portion that is pyramidal or tapered. Balloon 60e of FIG. 23B may also have a collar with a shaped portion that is pyramidal or tapered in the opposite direction as the taper of balloon 60d. Balloon 60f of FIG. 23C may have a collar with a shaped portion that is bulbous. In some embodiments, the shaped portion is part of the proximal elongated projecting portion 68 of the proximal collar 63. For example, FIG. 23A shows a proximal collar 63 with a proximal projecting portion 68 that projects into the operative channel 102 of the endoscope. In this embodiment, the shaped portion is tapered and located on the proximal projecting portion 68. The wider end of the taper is positioned adjacent the base portion 66 of the proximal collar 63. Alternatively, the narrower end of the taper may be positioned adjacent the base portion 66 as shown in FIG. 23B. In other embodiments, such as the one shown in FIG. 23C, the shaped portion may be bulbous. The bulbous shaped portion may be spaced from the base portion 66, as shown, or it may be positioned adjacent the base portion. FIG. 24 is a perspective view of a balloon with a tapered proximal projecting portion, similar to the embodiment of FIG. 23B. FIG. 25A is a side view of a balloon similar to FIG. 23B. In 25A, section lines are drawn along the proximal projecting portion 68. These section lines indicate the transverse cross-sectional views shown in FIGS. 25B-D.

Figure 26:
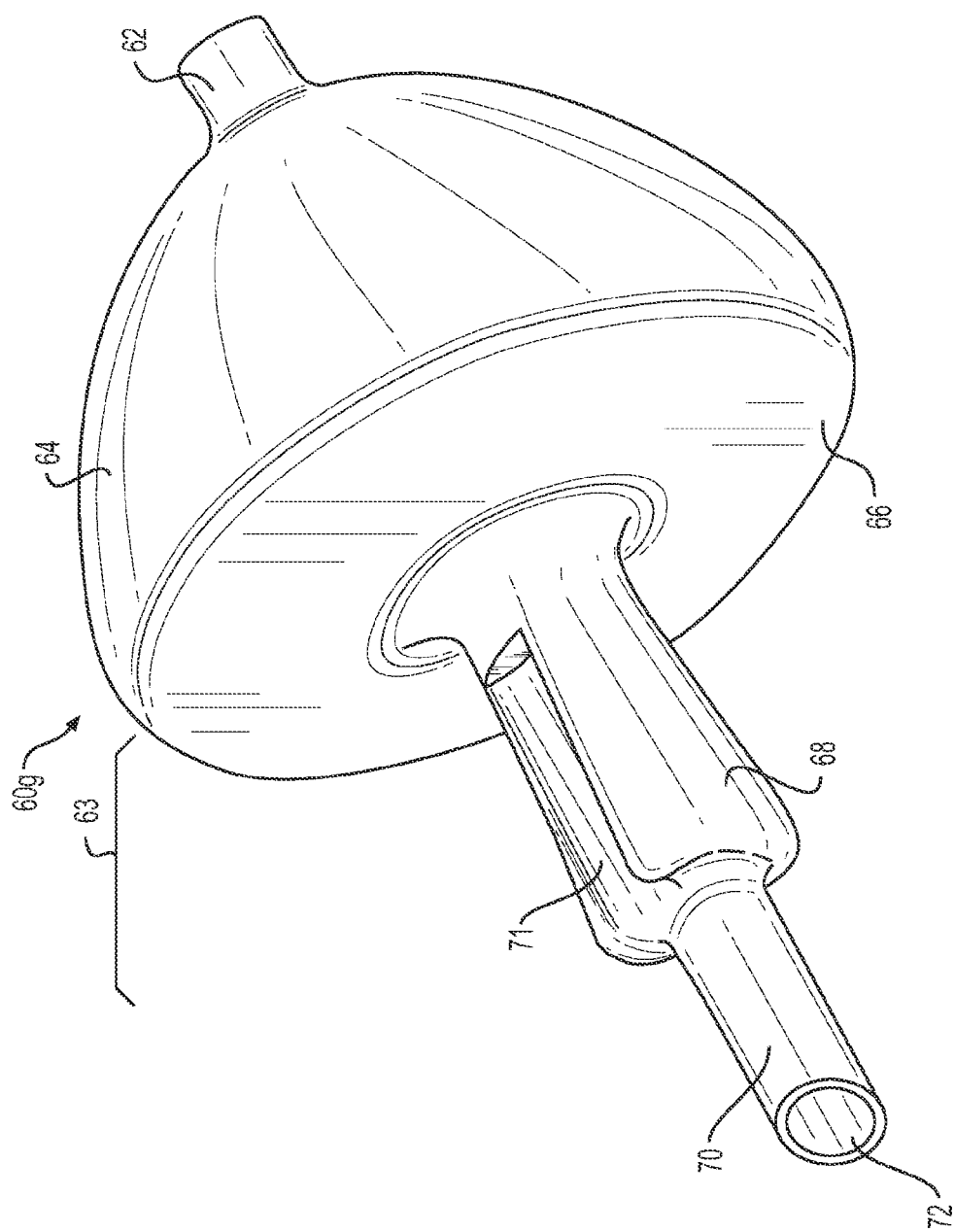
FIG. 26 is a perspective view of a balloon including longitudinal grooves.

FIG. 26 shows an embodiment of a balloon 60g configured for use with or without the cap 40. This embodiment includes a tapering shaped portion, similar to the embodiment of FIG. 24, as well as a longitudinal groove 71 on the proximal collar 63. The embodiment shown has one groove, but embodiments may have multiple grooves. For example, some embodiments may have 2, 3, 4, 5, 6, 7, 8, 9, or 10 grooves. The grooves 71 may extend only along the proximal projecting portion 68, or may start on the proximal projecting portion and continue along the base portion 66. The grooves may take various shapes when viewed in transverse cross-section. For example, the grooves 71 may be any polygonal shape, or the shape of a segment or sector of a circle or ellipse. For example, the grooves may be hemi-spherical or trapezoidal in shape. Alternatively, the grooves when viewed in transverse cross-section may have multiple portions, and each portion may take the shape of a polygon or a segment or sector of a circle or ellipse. In some embodiments, grooves 71 allow the user to eject fluid around the projecting portion 68 of the proximal collar 63 for assistance in cleaning the lens 105 while projecting portion 68 is inflated and abutting the walls of the operative channel 102. Alternatively, the grooves 71 may be used to activate a suction between the operative channel 102 of the endoscope and the intestinal environment.

Figure 27:
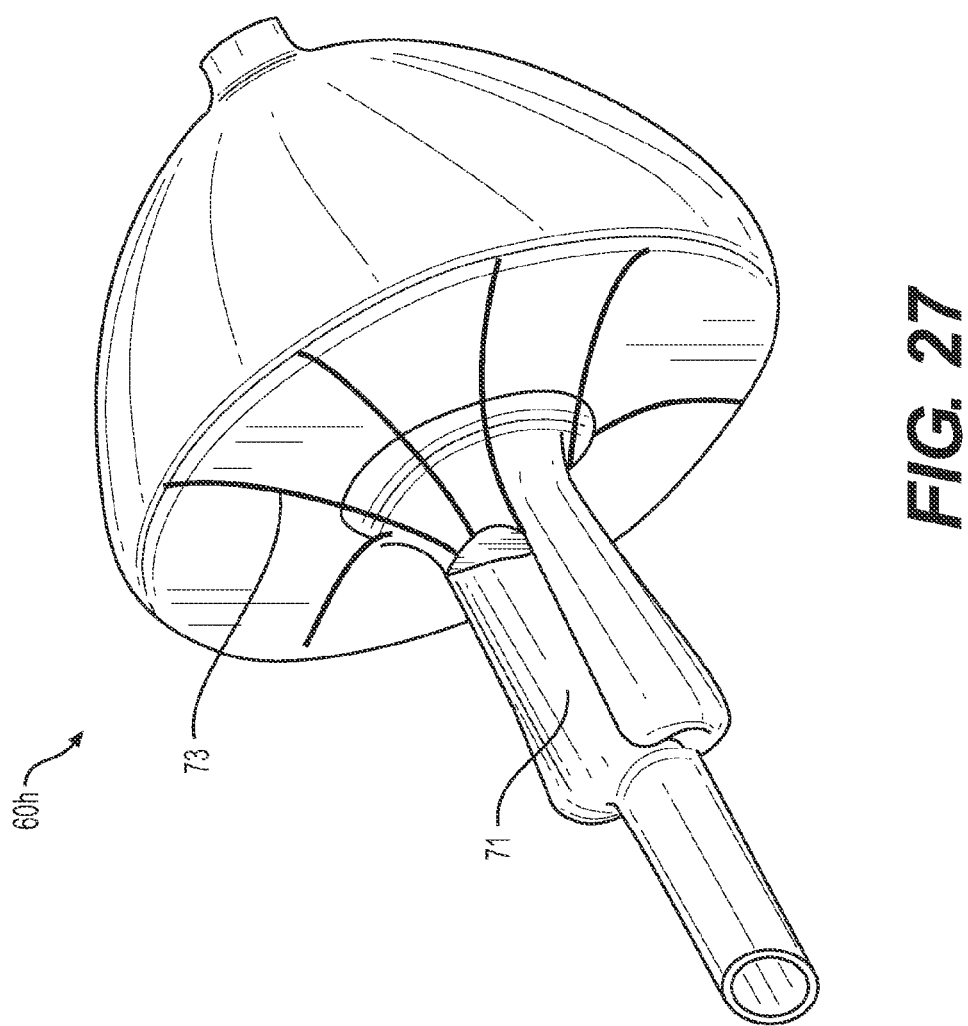
FIG. 27 is a perspective view of a balloon including longitudinal grooves and trusses.

FIG. 27 shows an embodiment of a balloon 60h configured for use with or without the cap 40. This embodiment includes a tapering shaped portion, similar to the embodiment of FIG. 24, and also includes longitudinal grooves 71 and trusses 73. The balloon may have multiple trusses, for example 2, 3, 4, 5, 6, 7, 8, 9, 10, 11, 12, 13, 14, 15, 16, 17, 18, 19, 20 or more trusses. The trusses 73 may be of any shape. For example, the trusses 73 may be cylindrical, ellipsoidal, or polygonal in shape. The trusses may extend from at least one proximal point to at least one distal point on the proximal collar 63. For example, trusses 73 may extend along only the proximal projecting portion 68, only along the base portion 66, or along both portions 66 and 68 of collar 63. The trusses may act as architectural reinforcements to stabilize the balloon, keeping it in contact with the distal face of the endoscope 104 and the lens 105.

The inclusion of grooves 71 or trusses 73 may give part of the proximal collar 63 a sun beams-shaped pattern when viewed in transverse cross-section (perpendicular to the longitudinal axis of the balloon). The rays of the sun beams shape are areas that thicken the wall of the balloon, such as the trusses 73 of the embodiment in FIG. 27. The sun beams-shaped pattern includes indentations between the rays. In some embodiments, these indentations may be grooves 71, or spaces between trusses 73. The indentations may be configured to engage at least one protrusion on an underlying surface, such as the distal face 104 or operative channel 102 of the endoscope 100. In some embodiments, the protrusion is the lens 105. The user may position the balloon to optimize visualization after inflation, for example by rotating the balloon such that an indentation mates with the lens 105. This allows the lens to image through a thinner area of the balloon wall, improving visualization of the intestinal structures.

FIGS. 28-33 depict attachable structures 40d-f for coupling to an endoscope. The attachable structures may optionally be used in conjunction with balloons, as seen in FIGS. 30A-B and 31A-B. The attachable structures may be attached at the distal end of an endoscope and used to contact the inflated balloon for the same reasons as described for seal caps 40 and 40a-c.

Endoscopes equipped with attachable structures may also be used without the balloons of the balloon access device. The attachable structures 40d-f have flexible appendages 47d-f that reduce looping of the intestine, especially in a non-insufflated intestine. When the practitioner pulls the endoscope back toward the opening of the bodily cavity, the attachable structures 40d-f move the intestinal wall relative to the imaging system, forming pleats. This movement reduces looping, improves efficiency, and results in a less painful endoscopic procedure for the patient. The attachable structures 40d-f may be positioned at the distal end of the endoscope or anywhere along the endoscope shaft.

As shown in FIGS. 28-33, the attachable structures 40 have a body 43 with an outer surface 74 and an inner surface 76 which defines a passageway for passage of an endoscope. The passageway has a proximal opening 57, a distal opening 59, and a central longitudinal axis A-A extending through the passage.

Figure 31A:
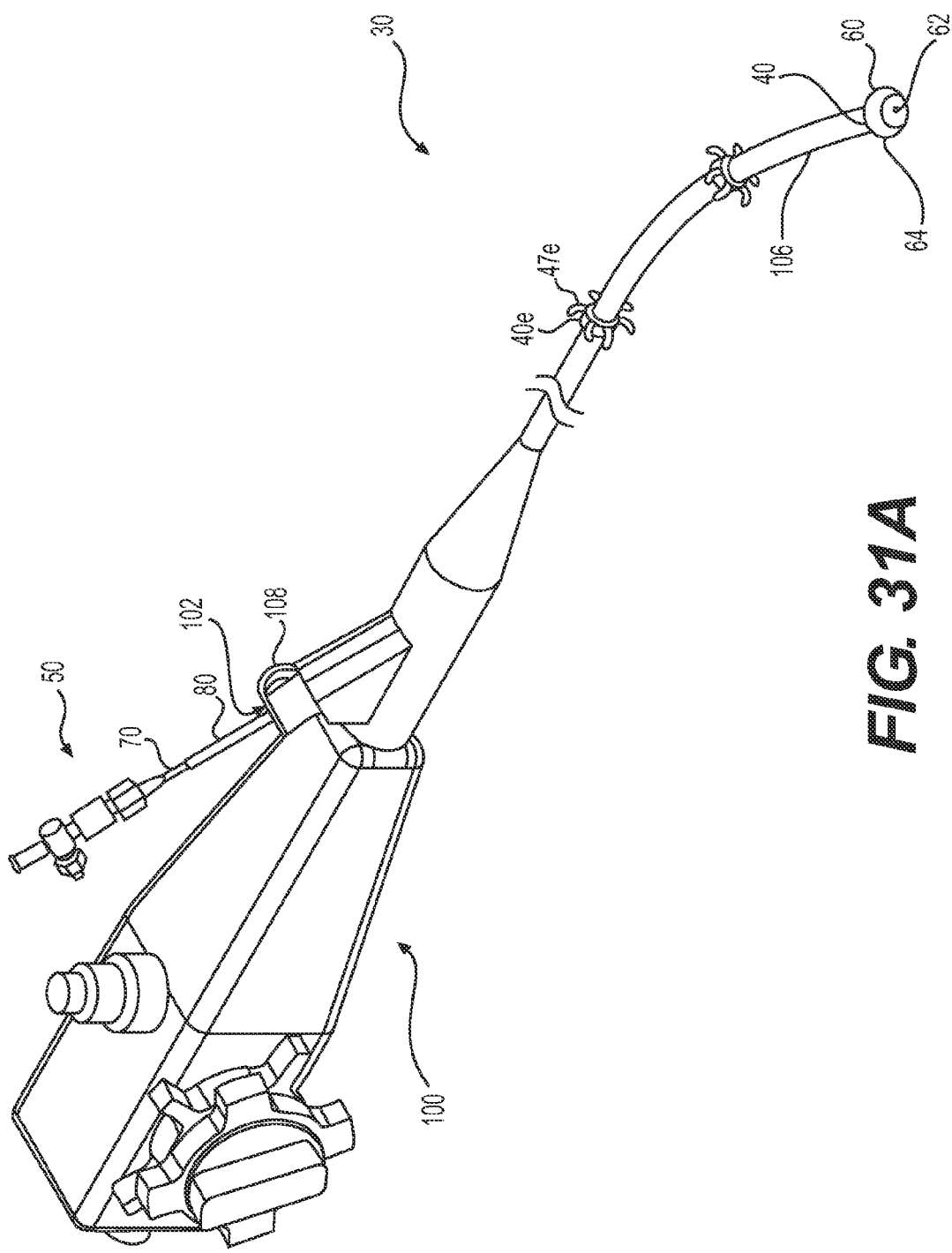
FIG. 31A is an isometric view of an endoscope and balloon access device utilizing attachable structures with flexible appendages.

The attachable structures may take various forms, and the various forms may be used in combination with each other. For example, some attachable structures may be caps configured to be coupled to the distal end of the endoscope, such as the seal caps 40 and 40a-c described in FIGS. 7-12. In FIGS. 31A-B, the balloon 60 is coupled to the distal end of the endoscope with a seal cap 40 (not visible from this angle).

Other attachable structure embodiments may be positioned along the shaft of the endoscope, such as attachable structures 40e shown in FIGS. 31A-B. In some embodiments, the attachable structure is tubular in nature and configured to extend 360 degrees around the shaft of the endoscope, as seen in FIGS. 31A-B. For example, the opening of the attachable structure may be a lumen. The attachable structure may also be flexible and configured to be stretched around the endoscope shaft.

Certain embodiments of attachable structures may extend around only a portion of the endoscope shaft, such as 90-360 degrees around the shaft. For example, the attachable structure may be a clip configured to be attached to the endoscope shaft, and extending partially or almost completely around the endoscope shaft. The clip may include a fastening mechanism, such as a hinge.

The attachable structures 40d-f may be positionable or movable along the endoscope shaft. For example, the body of one or more attachable structures may be slid, clipped, or rolled along the shaft of the endoscope as in FIG. 31A-B. Attachable structure 40e is shown in FIGS. 31A-B as an example, but other embodiments of attachable structures may also be movable along the endoscope shaft.

The attachable structures 40d-f may be separated along the endoscope shaft, as in FIG. 31A. In some embodiments, the attachable structures are spaced from each other a distance of 5, 10, 20, 30, 40, 50, 60, or 70 centimeters, or any distance between 5-70 centimeters. In other embodiments, such as the one shown in FIG. 31B, two or more attachable structures may be positioned adjacent another attachable structure, for example, with a spacing of 0-2 centimeters. This closer spacing forms one or more groupings of attachable structures. For example, in FIG. 31B, two groupings of 3 attachable structures 40e are shown positioned at different points along the endoscope shaft. In some embodiments, all of the attachable structures positioned along the endoscope shalt may be positioned adjacent each other, for example, with a spacing of 0-2 centimeters.

In the embodiment shown in FIG. 32, attachable structures 40e are attached to the outside of an elongate sheath 53. The sheath 53 is configured to fit tightly around the shaft of the endoscope 100. In some embodiments, the sheath 53 is a fabric or a mesh-like material as seen in FIG. 32. Attachable structures, such as 40d-f shown in FIG. 29A-C, may be affixed to the sheath 53 by a variety of fastening means. These fastening means include but are not limited to glue, bonding, sutures, stitches, or hook and loop fasteners. Alternatively, an attachable structure may take the form of an elongate sheath with multiple rows of flexible appendages.

FIG. 28A shows an exemplary attachable structure 40d having a body 43d with a proximal opening 57d, a distal opening 59d, and a longitudinal axis A-A extending between the openings. The length of (be attachable structure may be between 1-20 millimeters (as measured parallel to a longitudinal axis running from the proximal to the distal end). The opening may have a radius of 2-8 mm, or an area of 12-201 $mm^2$. The area of the opening may change at varying points between the proximal and distal ends, or it may stay constant.

Figure 33A:
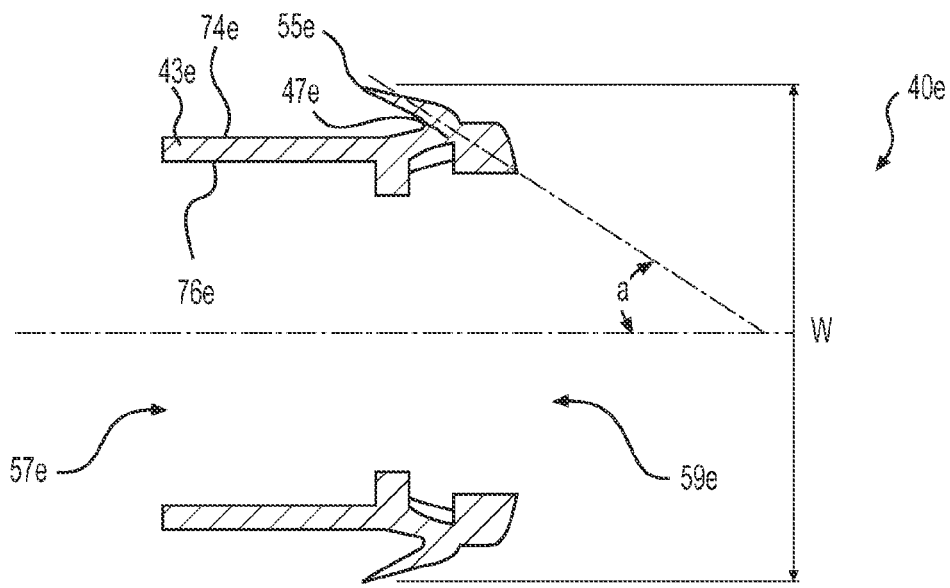
FIG. 33A is a side cross section of an attachable structure with appendages biased toward the proximal opening of the attachable structure body.
Figure 33B:
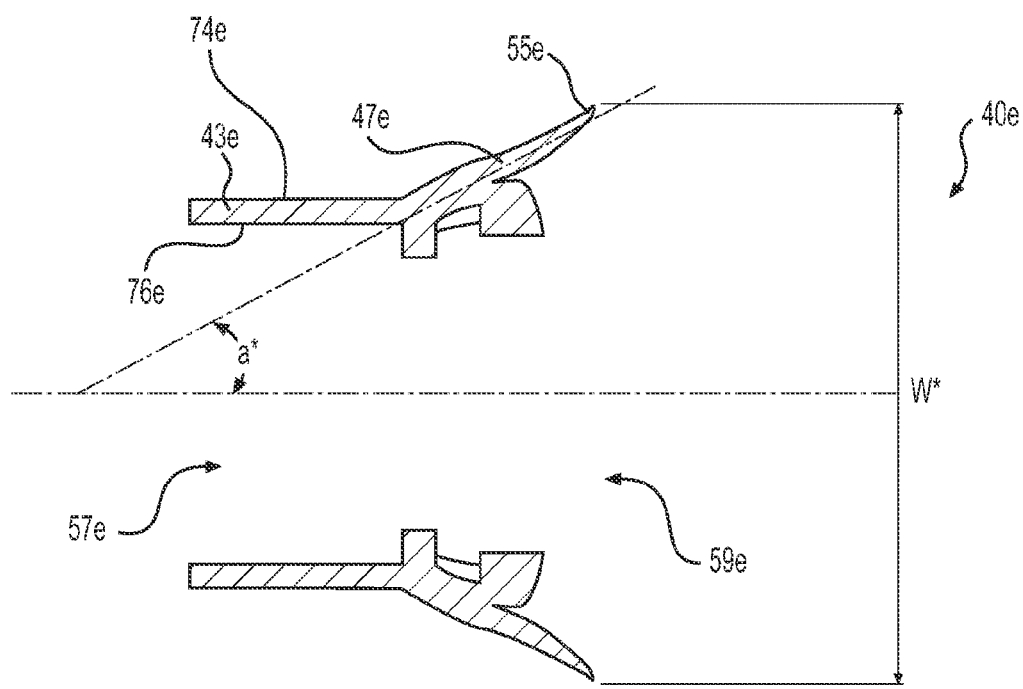
FIG. 33B is a side cross section of an attachable structure with flexible appendage tips pointing away from the proximal opening of the attachable structure body.
Figure 33C:
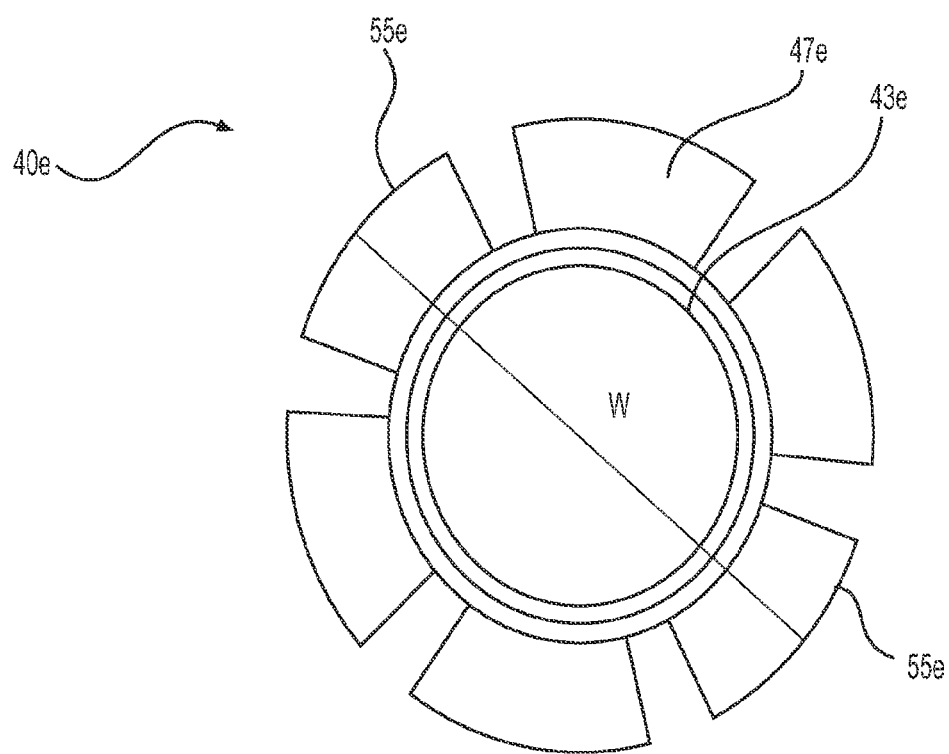
FIG. 33C is a tip view of an attachable structure demonstrating a greatest width w of the attachable structure as measured between the tips of opposite appendages.

As shown n FIGS. 33A-C, the attachable structures also have a width w measured perpendicular to the longitudinal axis. The greatest width of the attachable structure extends from the tip of a first flexible appendage 55 to the tip 55 of an appendage on the opposite side of the central longitudinal axis. The width, w, of the attachable structure may be 33 millimeters or less. The width w is substantially great enough to ensure contact with the walls of a non-insufflated intestine.

The exemplary attachable structures 40d-f shown in FIGS. 28-32 also include one or more flexible appendages 47d-f extending outwardly from the outer surface of the body 43d-f. As shown in FIG. 33A, the flexible appendages 47e may be biased toward the proximal opening 57e of the body, forming an acute angle, a, relative to the central longitudinal axis. For example, the flexible appendage may extend toward the proximal opening of the attachable structure at an angle a of up to 50 degrees relative to the central longitudinal axis. In one embodiment, the flexible appendage is biased toward the proximal opening at an angle a of 35 degrees. The bias may be manufactured during fabrication, not requiring compression within an intestine to achieve the acute angle.

As shown in FIG. 33B, the exemplary flexible appendages 47e are also configured to bend when retracted within an intestine, such that their tips 55e are pointing in a direction away from the proximal opening 57e of the body, the flexible appendages 47 in their bent position form a second acute angle a* relative to the longitudinal axis A-A of the body. When the flexible appendages are in their bent position, the width w* may be 33 millimeters or less. The lack of insufflation enables close contact between the appendages and the intestinal walls. When the surgeon pulls back on the endoscope, the intestine is pleated by the increased drag caused by the flexible appendages.

In some embodiments, the body and the flexible appendage of the attachable structure are made of the same material. For example, the body and the flexible appendages may be one continuous piece of material. In other embodiments, the materials may be different and may not be one continuous piece of material. In some embodiments, the body may be relatively less flexible than the at least one flexible appendage. The attachable structures may be formed of a thermoplastic elastomer, or, in some embodiments, silicone.

As shown in FIGS. 31A-B, the exemplary flexible appendages 47e may be aligned to each other with respect to their position along the length of the attachable structure 40e, forming a row. As shown in FIG. 28B, some attachable structure embodiments may include multiple rows of flexible appendages. For example, in FIG. 28B, the flexible appendage 47d belongs to a first row, and flexible appendages 49d and 51d belong to a second and third row of flexible appendages.

Figure 29A:
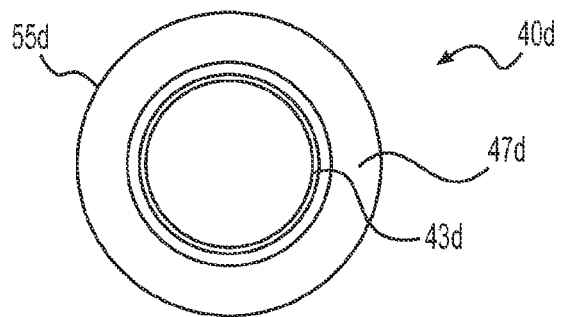
FIG. 29A is a top view of an attachable structure with a unitary flexible appendage.
Figure 29B:
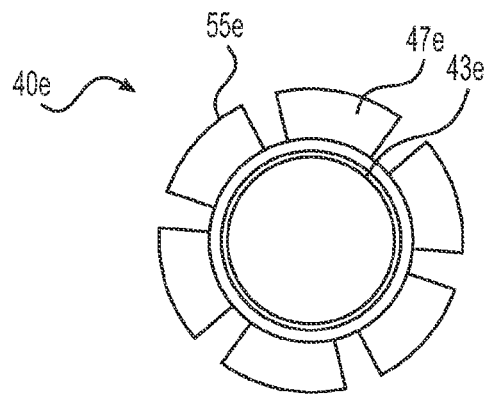
FIG. 29B is a top view of an attachable structure with multiple flexible appendages extending outwardly from the attachable structure.
Figure 29C:
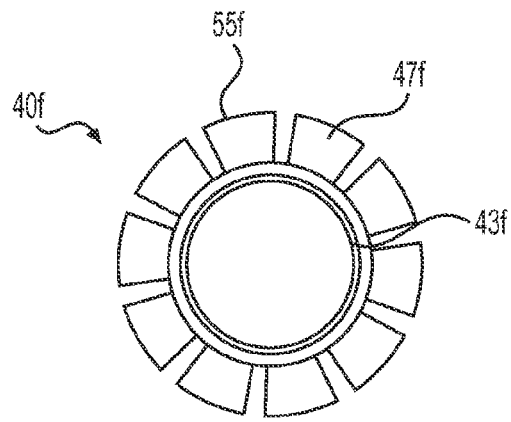
FIG. 29C is a top view of an attachable structure with multiple flexible appendages extending outwardly from the attachable structure.

The attachable structures may comprise one or more flexible appendages within the same row along the length of the attachable structure. For example, FIGS. 29A-C show three embodiments of attachable structures, 40d, 40e, and 40f. Some embodiments, such as 40d, may have just one flexible appendage 47d in one of the rows. That one appendage encircles the entire body 43d of the attachable structure. Alternatively, there may be multiple flexible appendages extending outward from the attachable structure within the same row. For example, in FIG. 28B, six flexible appendages 47e extend outward from the attachable structure 40e. In FIG. 29C, ten flexible appendages 47f extend outward from the attachable structure 40f. Some embodiments may comprise as many as 20 flexible appendages per row, including 1, 2, 3, 4, 5, 6, 7, 8, 9, 10, 11, 12, 13, 14, 15, 16, 17, 18, 19, or 20 appendages per row of flexible appendages. Other embodiments may have more than 20 flexible appendages per row. The number of flexible appendages may vary depending on the position of the row along the length of the attachable structure.

The flexible appendages may have a length of 1-5 millimeters extending from an outer surface of the attachable structure. In some embodiments of attachable structures, such as the one seen in FIG. 28B, the length of a flexible appendage 47d of a first row may be shorter than the lengths of the flexible appendages 49d and 51d of rows that are proximally spaced from the first row along the length of the attachable structure.

The flexible appendages 47 include base portions adjacent the body of the attachable structure and outer portions spaced outwardly from the base portion of the appendage. The outer portions culminate in appendage tips 55 as shown in FIGS. 33A-C. In some embodiments, the appendages are relatively flat. In the relatively flat embodiments, top and bottom faces may extend between the base portion and outer portion. The top face in these embodiments is oriented toward the distal opening of the body, and the bottom face is oriented toward the proximal opening.

In some embodiments, the flexible appendages may be fan shaped when viewed from the top as seen in FIG. 33C. In these embodiments, the width across the top face is narrower at the base portion of the appendage than the outer portion of the appendage. In some embodiments, the flexible appendages are relatively thin. For example, the width across the top face may be at least twice the distance as a thickness measured perpendicular to the top face. Exemplary flexible appendages may have a thickness between 0.1-0.9 millimeters, as measured perpendicularly from the top face of the appendage.

FIGS. 31A-B and FIG. 32 show embodiments where multiple attachable structures are positioned along the shaft of an endoscope. In these embodiments, the length of flexible appendages 47 of a distally spaced attachable structure 40 may be shorter than the lengths of flexible appendages of proximally spaced attachable structures. For example, the length of a flexible appendage may be 0.1-1 mm shorter than the flexible appendage of a proximally spaced attachable structure. In embodiments with groupings of attachable structures, such as the one shown in FIG. 31B, flexible appendages of the attachable structures of a distal grouping may be shorter than those of a proximally spaced grouping.

The endoscope equipped with attachable structures 40d-f may be used in methods of visualizing the internal surface of an intestinal cavity. As part of these methods, a practitioner attaches one or more attachable structures to an endoscope such that the attachable structure extends at least partially around the shaft of the endoscope as seen in FIGS. 31A-B. The exemplary attachable structures may be positioned at the distal end of the endoscope, such as attachable structure 40 in FIGS. 31A-B. The exemplary attachable structures may also be positioned along the endoscope shaft, such as attachable structures 40e in FIGS. 31A-B. After attachment, the flexible appendages 47e of the attachable structures face outwardly.

Figure 30A:
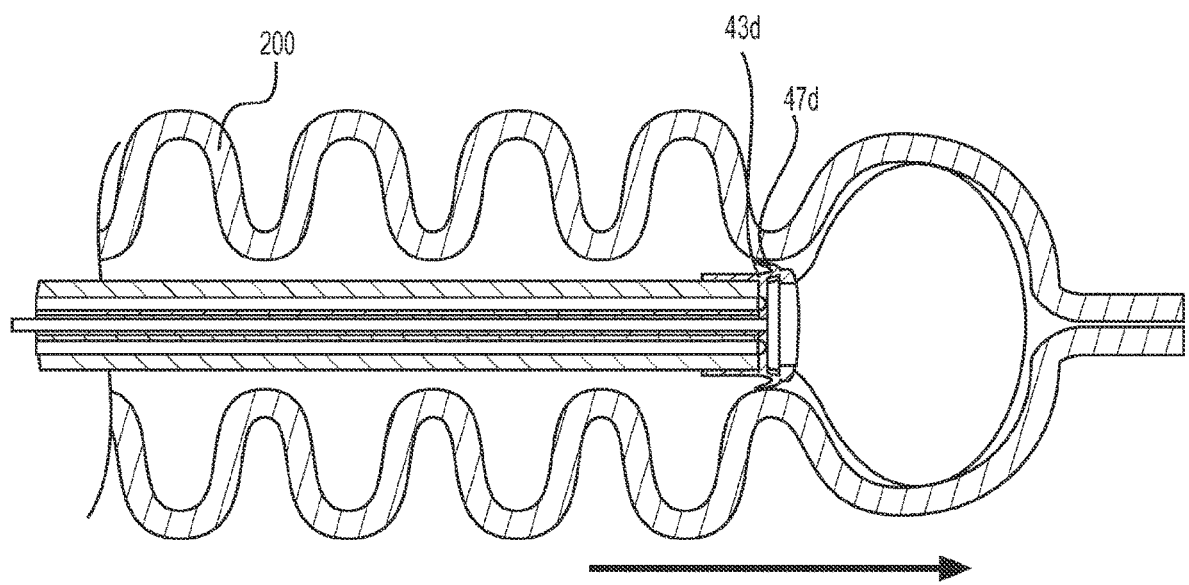
FIG. 30A is a cross section of an endoscope and balloon access device utilizing an attachable structure with flexible appendages. The endoscope is being pushed forward within a non-insufflated intestinal cavity.

As another part of these methods, the practitioner positions the endoscope equipped with attachable structures within an intestinal cavity of a subject, such that the one or more flexible appendages 47 contacts the intestinal wall. The practitioner pushes on the shaft of the endoscope to cause a forward advance of the endoscope. As the endoscope is pushed further into the intestinal cavity, the flexible appendages are oriented toward the proximal end of the structure in a relatively low resistance position, as seen in FIGS. 30A and 33A.

Figure 30B:
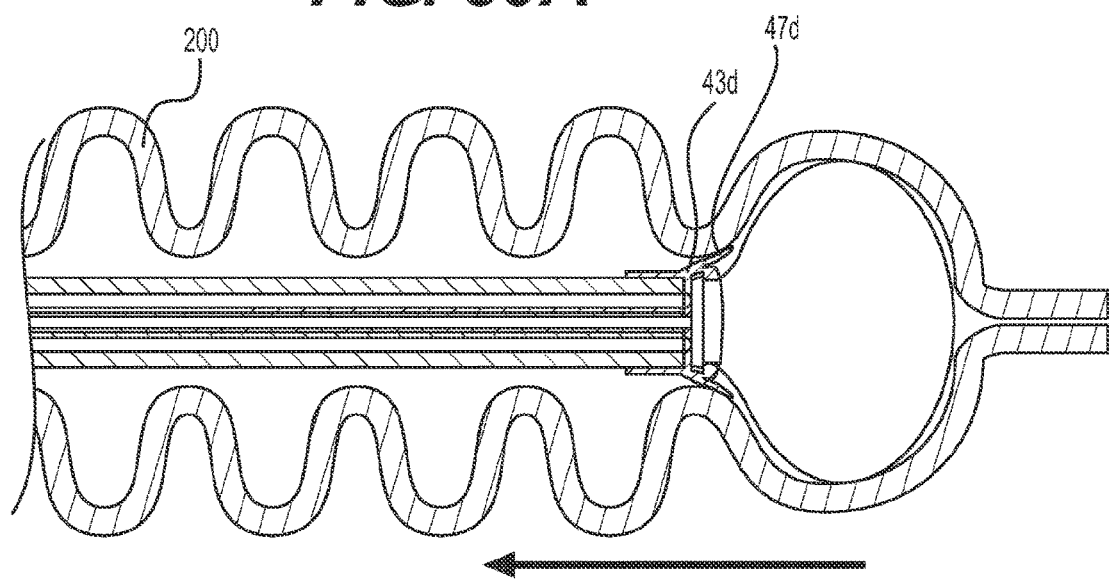
FIG. 30B is a cross section of an endoscope and balloon access device of FIG. 32A utilizing an attachable structure with flexible appendages. The endoscope is being pulled backward within a non-insufflated intestinal cavity.

The attachable structures 40d-f facilitate a forward advance of the endoscope by reducing intestinal looping. When the practitioner pulls back on the shaft of the endoscope, the flexible appendages 47 flip directions toward the distal opening of the attachable structure, as seen in FIGS. 30B and 33B. This is the relatively high resistance position of the flexible appendages. Pulling back on the shaft of the endoscope when the flexible appendage is in the high resistance position causes dragging of the intestinal wall 200, as seen in FIGS. 30A-B. This dragging changes the position of the intestine relative to the anus, and may create a pleated formation and reduce looping. The reduction in looping facilitates a forward advance of the endoscope. Upon the forward advance, the flexible appendage 47 flips back to its low resistance position.

The methods disclosed herein may be performed without insufflation of the intestinal cavity. The lack of insufflation promotes contact between the flexible appendages of the attachable structures and the intestinal wall 200, as seen in FIGS. 30A-B.

Attachable structures 40d-f may be attached to the endoscope in a variety of ways. In some embodiments, the practitioner may stretch the attachable structures around the distal end and the shaft of the endoscope. For example, when the attachable structure has a flexible, tubular body 43, it may be stretched around the distal end of the endoscope. The attachable structures may be positioned at the distal end of the endoscope, along the shaft, or both. If the attachable structure is a tubular, flexible embodiment, the practitioner may position it by rolling or sliding it proximally along the shaft, as seen in FIGS. 31A-B. Alternatively, the attachable structures may be clipped onto the shaft. In other embodiments, the attachable structures may be positioned along the shaft using sheath 53 shown seen in FIG. 32. For methods using this or similar embodiments, positioning one or more attachable structures along the shaft includes pulling the sheath 53 over the distal face of the endoscope.

The methods of visualizing the intestinal wall may also include balloon 60, as shown in FIGS. 31A-B. In embodiments of these methods, an attachable structure 40 adjacent the distal end of the endoscope is a cap configured to encircle the distal end of the endoscope. The cap contacts and secures the balloon when it is in its inflated state at over the imaging components of the endoscope. Activation of the imaging system causes light to be transmitted through the proximal and distal ends of balloon 60.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A system of an endoscope and at least two discretely spaced attachable structures for performing an endoscopy procedure without insufflation, the system comprising an assembly of attachable structures, including:
    a first, proximally positioned attachable structure, the first attachable structure being flexible, configured to be operatively attached in direct contact with a shaft of the endoscope, movable along the shaft of the endoscope, and positionable at a first location along the shaft of the endoscope;
    a second, distally positioned attachable structure, the second attachable structure being flexible, configured to be operatively attached in direct contact with the shaft of the endoscope, movable along the shaft of the endoscope, and positionable at a second location spaced distally from the first location and spaced from a distal end of the endoscope; and
    a length of at least 5 centimeters between the first, proximally positioned attachable structure and the second, distally positioned attachable structure;
    wherein the assembly of attachable structures pleats an intestine during the endoscopy procedure; and
    wherein each of the first and second attachable structures comprise:
        a body formed of a flexible material and having an inner surface and an outer surface, the inner surface defining a passageway for passage of the endoscope there through, the passageway having a proximal opening at a proximal end of the attachable structure, , a distal opening at a distal end of the attachable structure,, a central longitudinal axis extending through the passageway, and a length of 20 millimeters or less measured between the proximal opening and the distal opening; and
        a plurality of flexible appendages formed as continuous extensions of the body material, the plurality of flexible appendages extending outwardly from the outer surface of the body, extending from the distal edge of the attachable structure, and culminating in appendage tips;
        wherein the appendages in a first position bend at the distal end of the attachable structure to be biased toward the proximal opening of the body at a first acute angle relative to the longitudinal axis of the body; and
        wherein the appendages are movable to a second position with the appendage tips pointing away from the proximal opening of the body at a second acute angle relative to the longitudinal axis of the body.

2. The system of claim 1, further comprising a third attachable structure, wherein the third attachable structure is flexible, configured to be operatively attached in direct contact with the shaft of the endoscope, movable along the shaft of the endoscope, and positionable at a third location along the shaft of the endoscope, wherein the third attachable structure works together with the first attachable structure and the second attachable structure to pleat the intestine during the endoscopy procedure.

3. The system of claim 1, wherein the length between the first attachable structure and the second attachable structure is at least 10 centimeters.

4. The system of claim 1, further comprising at least one additional attachable structure, wherein the additional attachable structure is flexible, configured to be operatively attached in direct contact with the shaft of the endoscope, movable along the shaft of the endoscope, and positionable along the shaft of the endoscope, and wherein a total length of the system, as measured between a proximal edge of a proximal-most attachable structure and a distal edge of a distal-most attachable structure is at least 10 centimeters.

5. The system of claim 4, wherein the total length of the system is at least 20 centimeters.

6. The system of claim 1, wherein the flexible material is an elastomer.

7. The system of claim 6, wherein each attachable structure is sufficiently elastic and flexible to be rolled along the shaft of the endoscope.

8. The system of claim 6, wherein each attachable structure is sufficiently elastic and flexible to be stretched around a distal face of the endoscope and rolled along the shaft of the endoscope.

9. The system of claim 1, wherein the flexible appendages are fan shaped.

10. The system of claim 1, wherein an acute angle formed between the flexible appendages in the first position and the longitudinal axis of the body is less than 50 degrees.

11. The system of claim 1, wherein the greatest width of a selected one of the attachable structures measured perpendicular to the longitudinal axis and extending from a first appendage tip on one side of the longitudinal axis to a second appendage tip on the other side of the longitudinal axis is up to and including 33 millimeters.

12. The system of claim 1, wherein the flexible appendages have a thickness between 0.1-0.9 millimeters.

13. The system of claim 1, wherein the flexible appendages extend 1-5 millimeters from the outer surface.

14. The system of claim 1, wherein a width across a top face of a selected flexible appendage of the plurality of flexible appendages is at least twice the distance as a thickness of the selected flexible appendage, wherein the thickness is measured in a direction perpendicular to the top face.

15. A kit configured to be used with an endoscope to perform an endoscopy procedure without insufflation, the kit comprising:
- a first attachable structure, the first attachable structure being flexible, configured to be operatively attached in direct contact with a shaft of the endoscope, movable along the shaft of the endoscope, and positionable at a first location along the shaft of the endoscope; and
- a second attachable structure, the second attachable structure being flexible, configured to be operatively attached in direct contact with the shaft of the endoscope, movable along the shaft of the endoscope, and positionable at a second location spaced distally from the first location and spaced from a distal end of the endoscope;
- wherein the first and second attachable structures are configured to work together as an assembly to pleat an intestine during the endoscopy procedure when positioned along the shaft of the endoscope and spaced from each other by a length of at least 5 centimeters;
- wherein each of the first and second attachable structures comprise:
  - a body formed of a flexible material and having an inner surface and an outer surface, the inner surface defining a passageway for passage of the endoscope there through, the passageway having a proximal opening at a proximal end of the attachable structure, a distal opening at a distal end of the attachable structure, a central longitudinal axis extending through the passageway, and a length of 20 millimeters or less measured between the proximal opening and the distal opening; and
  - a plurality of flexible appendages formed as continuous extensions of the body material, the plurality of flexible appendages extending outwardly from the outer surface of the body, extending from the distal edge of the attachable structure, and culminating in appendage tips;
- wherein the appendages in a first position bend at the distal end of the attachable structure to be biased toward the proximal opening of the body at a first acute angle relative to the longitudinal axis of the body; and
- wherein the appendages are movable to a second position with the appendage tips pointing away from the proximal opening of the body at a second acute angle relative to the longitudinal axis of the body.

16. The kit of claim 15, further comprising a third attachable structure, wherein the third attachable structure is flexible, configured to be operatively attached in direct contact with the shaft of the endoscope, movable along the shaft of the endoscope, and positionable at a third location along the shaft of the endoscope.

17. The kit of claim 15, wherein the flexible material is an elastomer.

18. The kit of claim 15, wherein the flexible appendages are fan shaped.

19. The kit of claim 15, wherein the greatest width of a selected one of the attachable structures measured perpendicular to the longitudinal axis and extending from a first appendage tip on one side of the longitudinal axis to a second appendage tip on the other side of the longitudinal axis is up to and including 33 millimeters.

* * * * *

UNITED STATES PATENT AND TRADEMARK OFFICE
CERTIFICATE OF CORRECTION

PATENT NO. : 11,779,196 B2
APPLICATION NO. : 16/578693
DATED : October 10, 2023
INVENTOR(S) : Boris Reydel It is certified that error appears in the above-identified patent and that said Letters Patent is hereby corrected as shown below:

In the Claims

Claim 1, Column 24, Lines 1-4 reading:
"there through, the passageway having a proximal opening at a proximal end of the attachable structure, , a distal opening at a distal end of the attachable structure,, a central longitudinal axis"
Should read:
--there through the passageway having a proximal opening at a proximal end of the attachable structure, a distal opening at a distal end of the attachable structure, a central longitudinal axis--

Claim 1, Column 24, Lines 19-22 reading:
"wherein the appendages are movable to a second position with the appendage tips pointing away from the proximal opening of the body at a second acute angle relative to the longitudinal axis of the body."
Should read:
--wherein the appendages are movable to a second position with the appendage tips pointing away from the proximal opening of the body at a second acute angle relative to the longitudinal axis of the body;
wherein the flexible appendages extend 1-5 millimeters from the outer surface.--

Claim 13, Column 25, Lines 1-2 reading:
"13. The system of claim 1, wherein the flexible appendages extend 1-5 millimeters from the outer surface."
Should read:
--13. The system of claim 1, wherein the flexible appendages extend 2.5 millimeters from the outer surface.--

Claim 15, Column 26, Lines 16-19 reading:
"wherein the appendages are movable to a second position with the appendage tips pointing away from the proximal opening of the body at a second acute angle relative to the longitudinal axis of the body."

Signed and Sealed this
Twenty-fourth Day of September, 2024

Katherine Kelly Vidal
*Director of the United States Patent and Trademark Office*

Should read:

--wherein the appendages are movable to a second position with the appendage tips pointing away from the proximal opening of the body at a second acute angle relative to the longitudinal axis of the body; wherein the flexible appendages extend 1-5 millimeters from the outer surface.--